US012722008B2

(12) United States Patent
Widge et al.

(10) Patent No.: US 12,722,008 B2
(45) Date of Patent: Sep. 1, 2026

(54) METHODS AND APPARATUS FOR RESTORATION OF BRAIN NETWORK ACTIVITY

(71) Applicants: REGENTS OF THE UNIVERSITY OF MINNESOTA, Minneapolis, MN (US); ECOLE POLYTECHNIQUE FEDERALE DE LAUSANNE (EPFL), Lausanne (CH); CORNELL UNIVERSITY, Ithaca, NY (US)

(72) Inventors: Alik Widge, Minneapolis, MN (US); Gregory Molnar, Minneapolis, MN (US); Virginia Woods, Minneapolis, MN (US); Mahsa Shoaran, Lausanne (CH); Uisub Shin, Lausanne (CH)

(73) Assignees: Regents of the University of Minnesota, Minneapolis, MN (US); Ecole Polytechnique Federale De Lausanne (EPFL), Lausanne (CH); Cornell University, Ithaca, NY (US)

( * ) Notice: Subject to any disclaimer, the term of this patent is extended or adjusted under 35 U.S.C. 154(b) by 220 days.

(21) Appl. No.: 18/274,345

(22) PCT Filed: Jan. 26, 2022

(86) PCT No.: PCT/US2022/013914
§ 371 (c)(1),
(2) Date: Jul. 26, 2023

(87) PCT Pub. No.: WO2022/164911
PCT Pub. Date: Aug. 4, 2022

(65) Prior Publication Data

US 2024/0100337 A1 Mar. 28, 2024

Related U.S. Application Data

(60) Provisional application No. 63/141,628, filed on Jan. 26, 2021, provisional application No. 63/141,633, filed on Jan. 26, 2021.

(51) Int. Cl.
*A61N 1/36* (2006.01)
*A61B 5/00* (2006.01)
(Continued)

(52) U.S. Cl.
CPC ............ *A61N 1/3606* (2013.01); *A61B 5/374* (2021.01); *A61B 5/4836* (2013.01);
(Continued)

(58) Field of Classification Search
CPC ................ A61N 1/3606; A61N 1/0529; A61N 1/36082; A61N 1/36125; A61N 1/36135;
(Continued)

(56) References Cited

U.S. PATENT DOCUMENTS 7,917,221 B2 3/2011 Tass
9,895,077 B2 2/2018 Shahaf et al.
(Continued)

FOREIGN PATENT DOCUMENTS

CN 109893125 A 6/2019
WO 2020095111 A1 5/2020

OTHER PUBLICATIONS

Anonymous, Phasor, Wikipedia, Dec. 16, 2020, XP 093225724, Retrieved from the Internet: URL: https://en.wikipedia.org/w/index.php?title=Phasor&oldid=994547264, retrieved on Jan. 27, 2025 [7 pgs.].

(Continued)

*Primary Examiner* — Paula J Stice
(74) *Attorney, Agent, or Firm* — QUARLES & BRADY LLP

(57) ABSTRACT

A method for controlling connectivity between two or more brain regions of a subject includes receiving signals corresponding to a connectivity between two or more regions of a subject's brain, measuring a connectivity level from the signals, and delivering at least one stimulation pulse to at
(Continued)

least one target region of the subject's brain if the measured connectivity level is outside of a predetermined range.

11 Claims, 21 Drawing Sheets

(51) Int. Cl.
*A61B 5/374* (2021.01)
*A61N 1/05* (2006.01)

(52) U.S. Cl.
CPC ....... *A61N 1/0529* (2013.01); *A61N 1/36082* (2013.01); *A61N 1/36125* (2013.01); *A61N 1/36135* (2013.01); *A61N 1/36139* (2013.01); *A61N 1/36178* (2013.01)

(58) Field of Classification Search
CPC ............ A61N 1/36139; A61N 1/36178; A61N 1/0534; A61B 5/374; A61B 5/4836; A61B 5/7253
See application file for complete search history.

(56) References Cited

U.S. PATENT DOCUMENTS

2005/0141642 A1 6/2005 Asami
2008/0109189 A1 5/2008 Bauer et al.
2009/0157141 A1 6/2009 Chiao et al.
2012/0271374 A1* 10/2012 Nelson ............... A61N 1/36082 607/45
2013/0342506 A1 12/2013 Westhues et al.
2014/0163627 A1* 6/2014 Starr .................. A61M 5/1723 607/45
2015/0119689 A1 4/2015 Pascual-Leone et al.
2015/0231397 A1 8/2015 Nudo, Jr. et al.
2016/0220836 A1* 8/2016 Parks ..................... A61N 2/006
2017/0068885 A1 3/2017 Alvarez-Icaza et al.
2017/0128729 A1 5/2017 Netoff et al.
2018/0110991 A1 4/2018 Molnar et al.
2019/0083805 A1 3/2019 Etkin
2019/0143119 A1 5/2019 Dzirasa et al.
2019/0247661 A1* 8/2019 Eskandar ............. A61N 1/0534
2019/0321638 A1 10/2019 Mogul
2020/0015692 A1 1/2020 Genov et al.
2020/0086120 A1 3/2020 Levy et al.
2020/0360695 A1* 11/2020 Widge ............... A61N 1/37288

OTHER PUBLICATIONS

Sreeraman, et al., Efficient Approximations for the Actangent Function, Retrieved from the Internet: URL: https://www-labs.iro.umontreal.ca/~mignotte/IFT2425/Documents/EfficientApproximationArctgFunction.pdf, retrieved on Jan. 27, 2025 [4 pgs].

Velarde, et al., Bifurcation structure determines different phase-amplitude coupling patterns in the activity of biologically plausible neural networks, Neurolmage 202 (2019) 116031, Neuroimage, Elsevier, Amsteram, NL XP085875783, ISSN: 1053-8119 [20 pgs].

Lei, et al., A Decade of Vector Fitting Development: Applications on Signal/Power Integrity, 2010, Retrieved from the Internet, URL: https://www.semanticscholar.org/paper/A-Decade-of-Vector-Fitting-Development%3A-on-Lei-Want/d817883dce10eb3608077e8e7ee41b09a34cc63e, retrieved on Jan. 27, 2025 [15 pgs].

International Search Authority—U.S., International Search Report and Written Opinion for corresponding International Application No. PCT/US2022/013916, mailed Apr. 12, 2022 [13 pgs.].

European Patent Office, Supplementary European Search Report, for corresponding European Patent Application No. 22746535.8, mailed Apr. 28, 2025 [15 pgs].

European Patent Office, Extended European Search Report issued for related European Patent Application No. 22746534.1, dated Nov. 18, 2024 [9 pgs.].

* cited by examiner

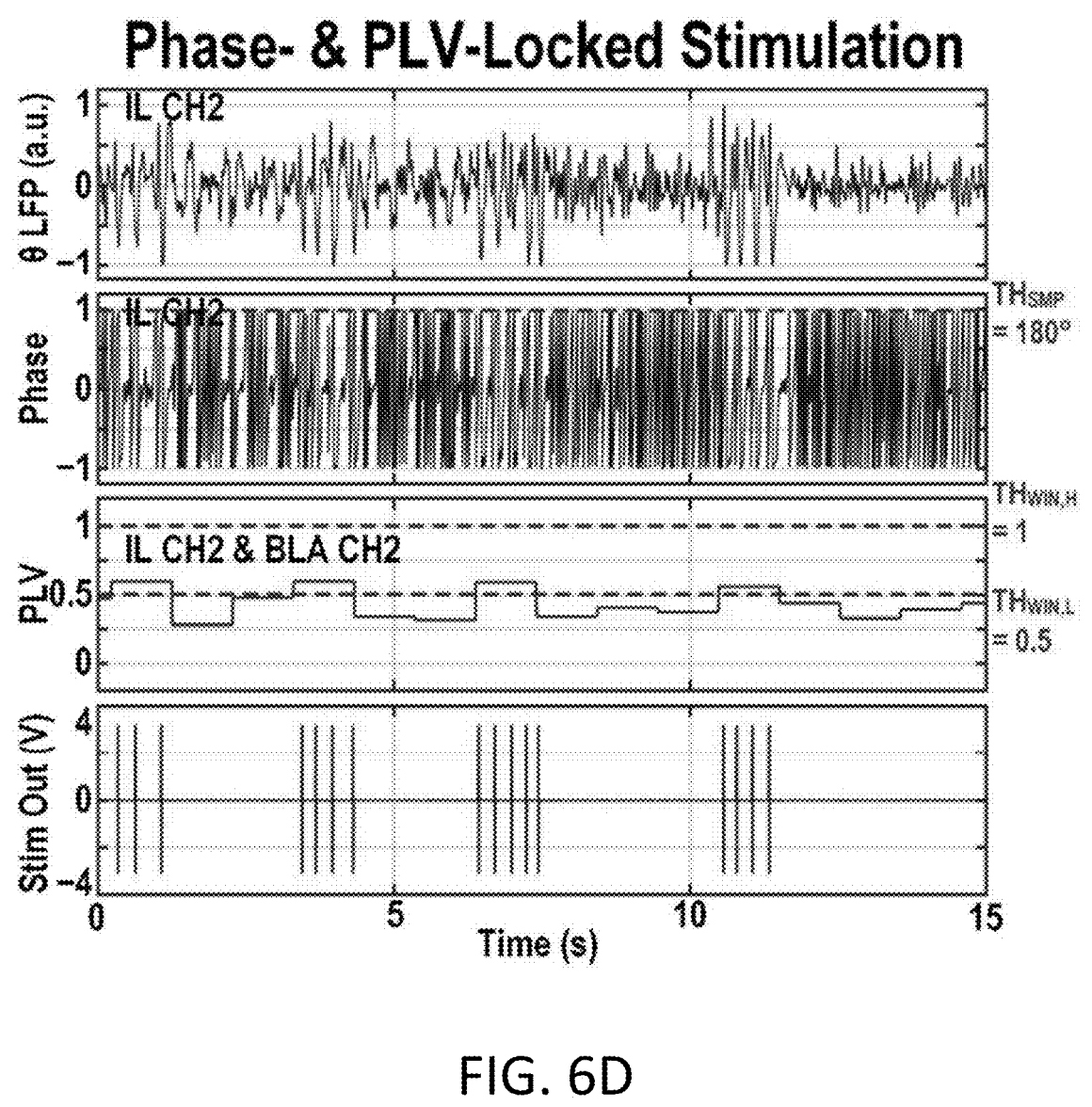

Phase- & PLV-Locked Stimulation

θ LFP (a.u.)
IL CH2
1
0
−1

Phase
IL CH2
1
0
−1
$TH_{SMP}$ = 180°

PLV
IL CH2 & BLA CH2
1
0.5
0
$TH_{WIN,H}$ = 1
$TH_{WIN,L}$ = 0.5

Stim Out (V)
4
0
−4

0 5 10 15
Time (s)

FIG. 6D

| Quadrants | $\frac{1}{\pi}\tan^{-1}\frac{Im}{Re}$ | Offset | Fraction |
|---|---|---|---|
| I | $0+\frac{Im}{4Re}$ | 0 | $\frac{Im}{4Re}$ |
| II | $\frac{1}{2}-\frac{Re}{4Im}$ | $\frac{1}{2}$ | $-\frac{Re}{4Im}$ |
| III | $sign(Im)\cdot 1+\frac{Im}{4Re}$ | $sign(Im)\cdot 1$ | $\frac{Im}{4Re}$ |
| IV | $-\frac{1}{2}-\frac{Re}{4Im}$ | $-\frac{1}{2}$ | $-\frac{Re}{4Im}$ |

| Metric | Ideal Features | Approximated Features |
| --- | --- | --- |
| Sensitivity (%) | 92.5 ± 10.2 | 93.7 ± 10.3 |
| FDR (# / hour) | 0.47 ± 0.55 | 0.73 ± 1 |
| PAC Correlation (%) | 95.4 ± 2.67 | |
| PLV Correlation (%) | 98.9 ± 0.52 | |

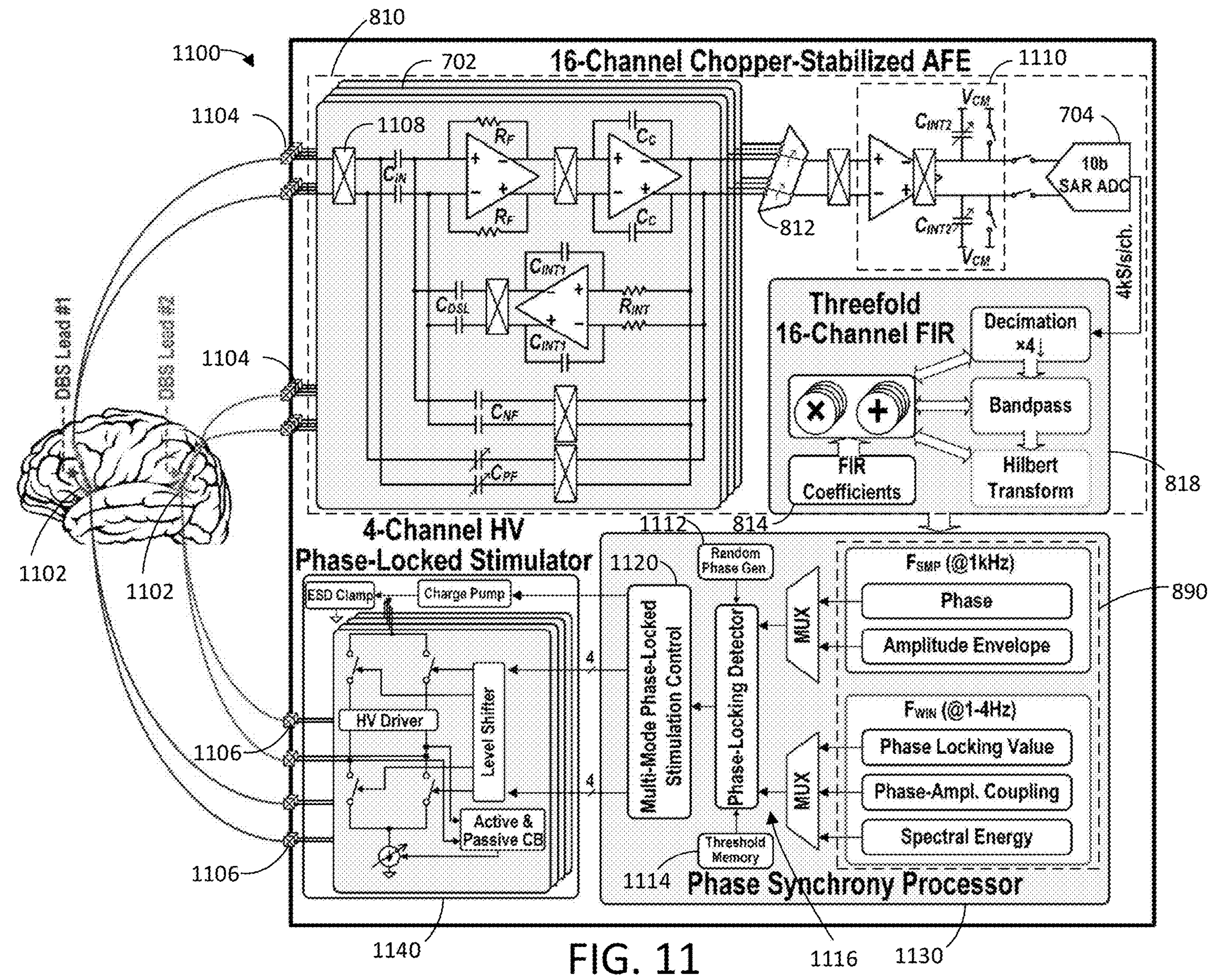
1100
810
702
16-Channel Chopper-Stabilized AFE
1110
1104
1108
704
10b SAR ADC
812
4kS/s/ch.
Threefold 16-Channel FIR
Decimation ×4
Bandpass
Hilbert Transform
FIR Coefficients
818
1104
DBS Lead #1
DBS Lead #2
1102
1102
4-Channel HV Phase-Locked Stimulator
1112
814
1120
Random Phase Gen
890
ESD Clamp
Charge Pump
$F_{SMP}$ (@1kHz)
Phase
Amplitude Envelope
MUX
Multi-Mode Phase-Locked Stimulation Control
Phase-Locking Detector
HV Driver
Level Shifter
$F_{WIN}$ (@1-4Hz)
Phase Locking Value
Phase-Ampl. Coupling
Spectral Energy
1106
Active & Passive CB
Threshold Memory
1106
1114
Phase Synchrony Processor
1140
1116
1130
FIG. 11

FIG. 15A
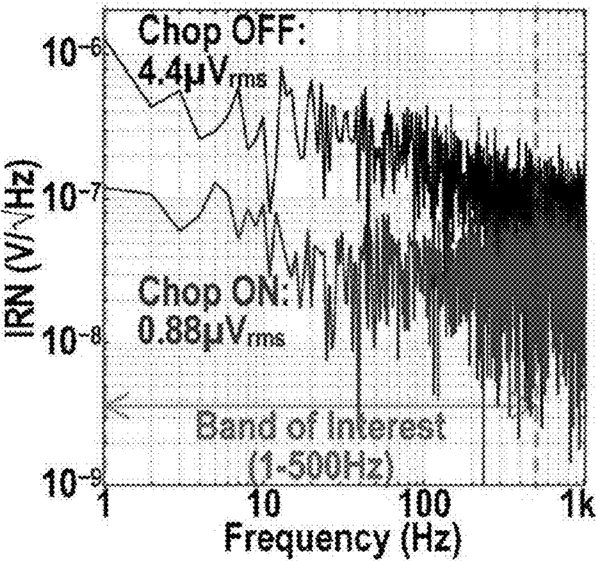
FIG. 15B
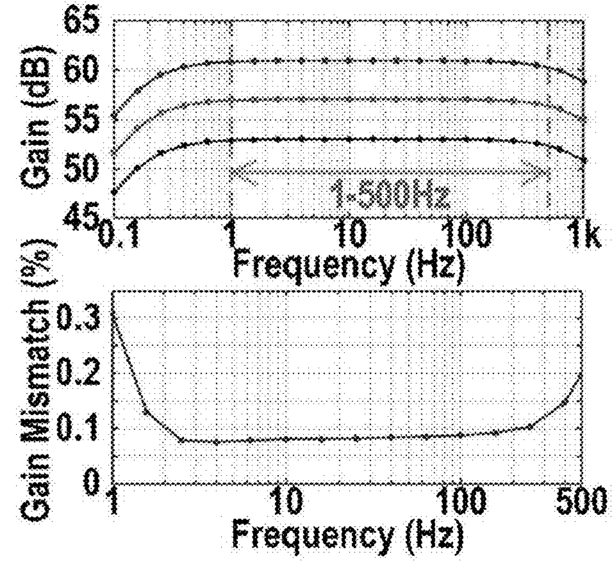
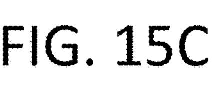
FIG. 15C
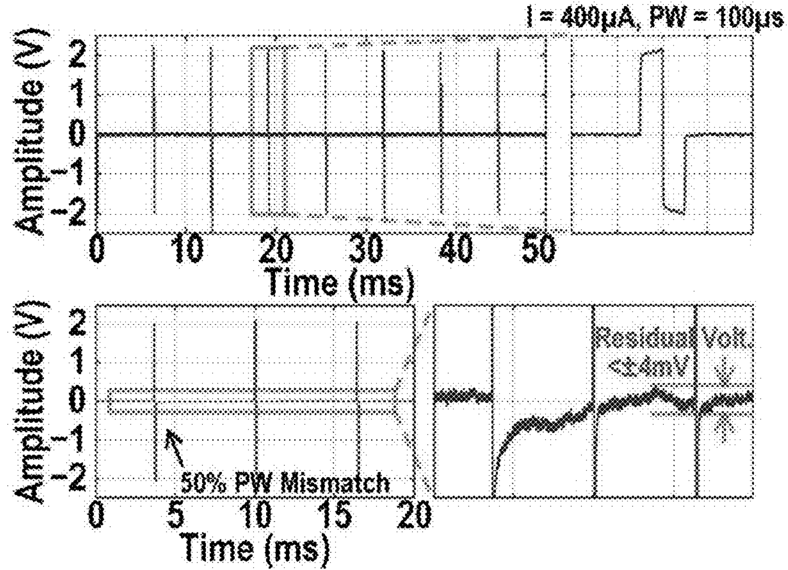

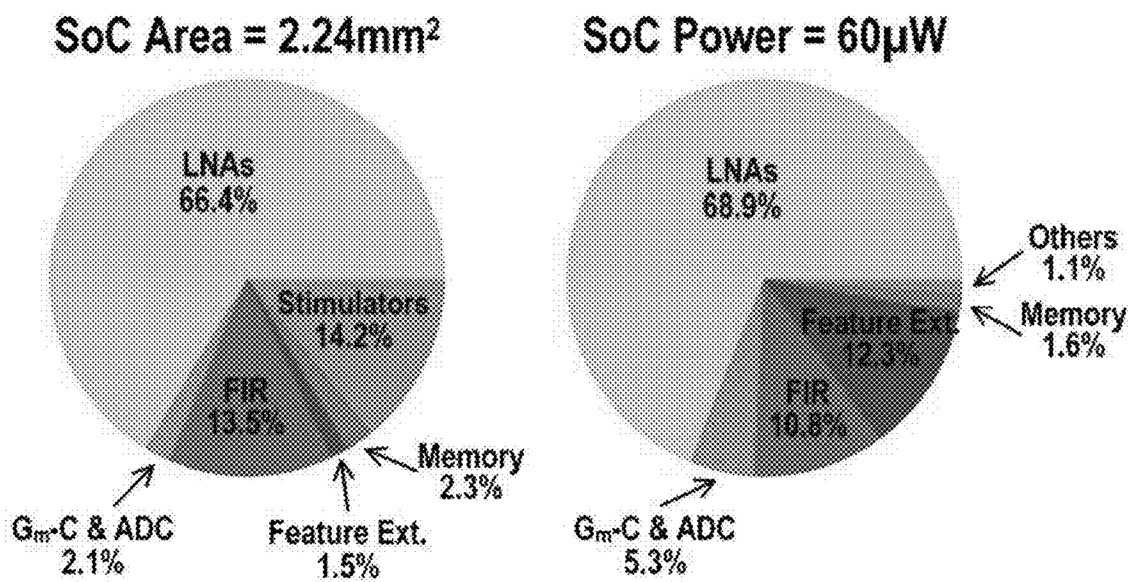

| Parameter | Example 1 | Example 2 | Example 3 | ASIC 1100 |
|---|---|---|---|---|
| Process (nm) | 180 | 130 | 130 | **65** |
| Supply Voltage (V) | 0.5 | 1.2 | 1.2 | **1.2/0.85** |
| # Recording Ch. | - | 64 | 32 | **16** |
| # Stimulation Ch. | - | 64 | 32 | **4** |
| SoC Area/ch.† ($mm^2$) | 0.025† | 0.109* | 0.237 | **0.14** |
| SoC Power (μW) | 0.015† | 1286* | 674‡ | **60** |
| PLV/PAC power (μW) | 0.015 (1 PLV w/ min detect.) | 400 (32 PLVs) | 200.4 (65 CFC/PLVs)^ | **9.69 (8 PAC/PLVs)** |
| Stimulation Modes | - | PLV thresholding | SVM Classification (PLV, CFC, SE) | **Phase (fixed/random), Ampl., PLV, PAC, SE thresholding** |

† Estimated based on # of recording channels

* Estimated from breakdowns excluding TX

‡ Digital back-end only

^ Estimated # of feature extractions

FIG. 16

METHODS AND APPARATUS FOR RESTORATION OF BRAIN NETWORK ACTIVITY

CROSS-REFERENCE TO RELATED APPLICATIONS

The present application is based on, claims priority to, and incorporates herein by reference in their entirety U.S. Provisional Patent Application No. 63/141,633, filed on Jan. 26, 2021, and entitled "Methods and Apparatus for Restoration of Brain Network Activity" and U.S. Provisional Patent Application No. 63/141,628, filed on Jan. 26, 2021, and entitled "Systems and Methods for Energy-Efficient Measurement of Neurophysiological Oscillations."

GOVERNMENT RIGHTS STATEMENT REGARDING FEDERALLY SPONSORED RESEARCH

This invention was made with government support under MH123634 awarded by the National Institutes of Health. The government has certain rights in the invention.

BACKGROUND

The present disclosure generally relates to monitoring and stimulating a subject's brain. Conventional neuromodulation devices and therapies are open-loop and do not target brain oscillations in a targeted, responsive, and on-demand way.

SUMMARY

According to one aspect of the present disclosure, a method for controlling connectivity between two or more brain regions of a subject is provided. The method can include receiving signals corresponding to a connectivity between a first target region and a second target region a subject's brain, determining, from the received signals, a connectivity level between the first target region and the second target region, and delivering at least one stimulation pulse to at least one of the first and second target regions if the connectivity level is outside of a predetermined range.

According to another aspect, the present disclosure provides a stimulation system for controlling connectivity between two or more brain regions of a subject. The system can include a first stimulation electrode configured for placement within a first target region and a second stimulation electrode configured for placement within a first target region, and a controller in communication with the first and second stimulation electrodes to monitor activity in the first and second target regions. The controller includes a processor configured to determine, from signals received from the first and second stimulation electrodes, a phase and amplitude of the signals in a first target region and a second target region within a predetermined frequency band, determine, from the phase of the signals, a connectivity level between the first target region and the second target region, and determine if the connectivity level is within a predetermined range. In response to determining that the connectivity level is outside of the predetermined range, the processor is configured to command at least one of the first and second stimulation electrodes to deliver at least one stimulation pulse.

In accordance with one aspect of the disclosure, a method for measuring and controlling connectivity between two or more brain regions of a subject is provided. The method comprises receiving signals corresponding to a connectivity between two or more regions of a subject's brain, measuring a connectivity level from the received signals, and delivering at least one stimulation pulse to at least one target region of the subject's brain if the measured connectivity level is outside of a predetermined therapeutic range.

The foregoing and other advantages of the present disclosure will appear from the following description.

BRIEF DESCRIPTION OF THE DRAWINGS

The present invention will hereafter be described with reference to the accompanying drawings, wherein like reference numerals denote like elements.

FIG. 6D illustrates the extraction of phase, calculation of PLV, and stimulation based on the phase and PLV in accordance with the systems and methods described herein.

FIG. 11 depicts an application specific integrated circuit according to one aspect of the present disclosure.

FIG. 15A depicts experimental measurements of input-referred noise according to one aspect of the present disclosure.

FIG. 15B depicts experimental measurements of gain and gain mismatch according to one aspect of the present disclosure.

FIG. 15C depicts experimental measurements of stimulation according to one aspect of the present disclosure.

FIG. 16 depicts area and power comparisons for an application specific integrated circuit according to one aspect of the present disclosure.

DETAILED DESCRIPTION

Figure 1:
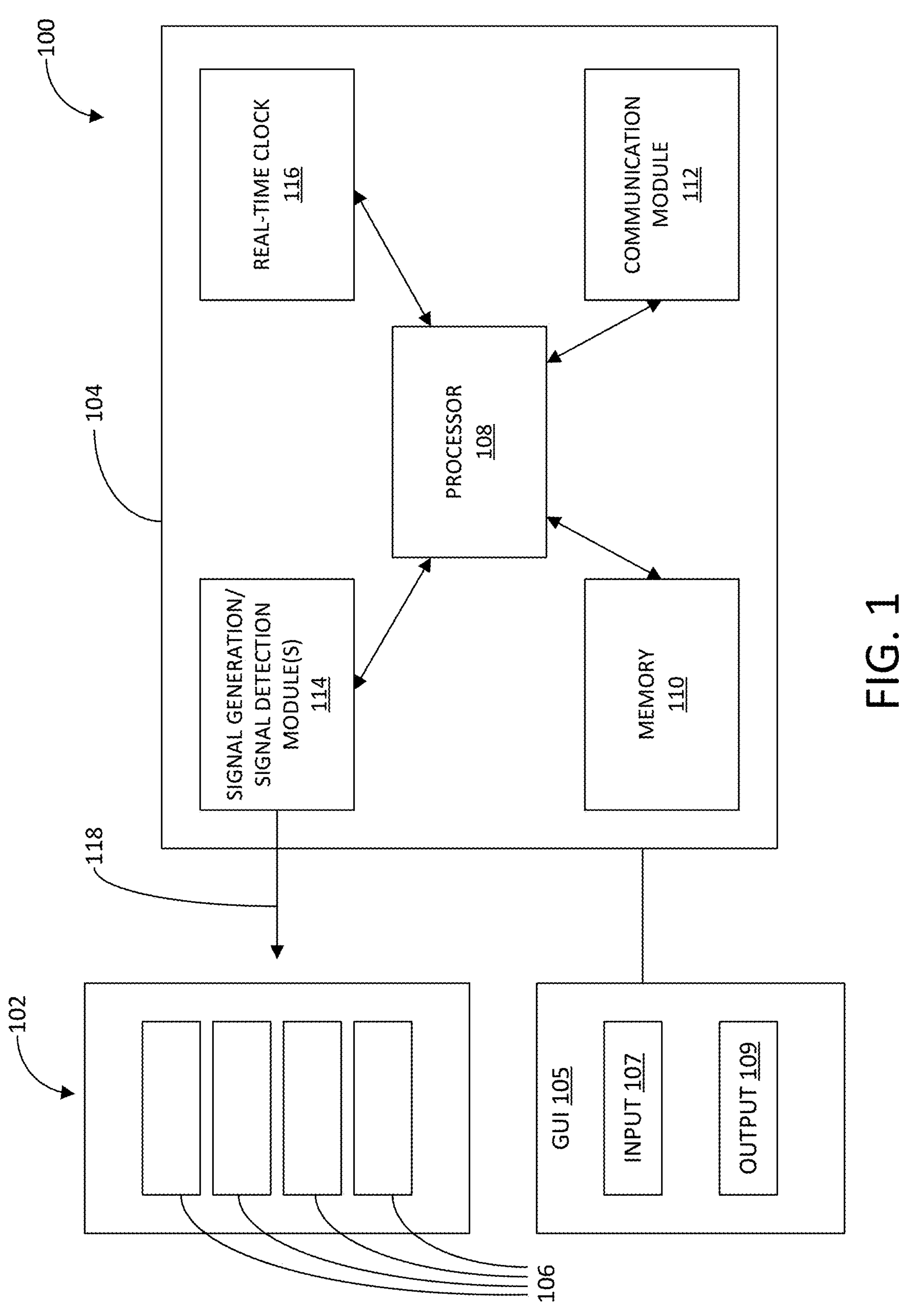
FIG. 1 is a block diagram of an exemplary stimulation system in accordance with an embodiment.

Clinical treatments of psychiatric conditions related to faulty brain circuit connectivity, such as mental health conditions including depression, post-traumatic stress disorder ("PTSD"), and addictions, are limited due to the lack of established treatment paradigms and appropriate deep brain stimulation ("DBS") devices. In particular, synchronized neural activity can be an important mechanism for communication between brain networks. These networks, however, are often impaired by the aforementioned psychiatric disorders, among other (e.g., autism, obsessive compulsive disorder, and the like). It is recognized herein that deep brain stimulation (DBS) can be utilized to address these, and other disorders.

As such, the present disclosure provides systems and methods for controlling brain activity using stimulation, such as electrical stimulation. In particular, a novel approach is introduced whereby a closed-loop and on demand implantable neuromodulation system and method can be used to treat neurological, psychological, and other connectivity-related brain conditions. The neuromodulation system senses brain activity, such as connectivity (e.g., synchrony) between two or more regions of a subject's brain, and delivers bursts or pulses of brain stimulation. The brain stimulation can be linked with precise (e.g., sub-millisecond) timing relative to ongoing neural events, such as the phase of ongoing oscillations in one or more areas or bursts of neural activity in one or more areas.

As will be described, connectivity between different regions of a subject's brain can be monitored and modified to restore an out-of-range connectivity level and return the connectivity level within a predetermined therapeutic range. Specifically, a stimulation pulse, train of pulses, paired pulse, or train of paired pulses can be delivered to one or more regions of the brain based on the connectivity level between two or more regions of the brain. Coherence or other indicators quantifying a connectivity between the two regions may be increased, decreased, or show changes in the signal variability over time. As used herein, "connectivity" can encompass synchrony metrics such as phase-amplitude coupling ("PAC"), phase-phase coupling (phase-locking value "PLV", coherence, phase lag index "PLI"), amplitude-amplitude coupling, or similar generalizations of correlation and cross-spectral operators. In another non-limiting example, connectivity may be defined as an active measurement performed by injecting a perturbation into one or more brain regions (e.g., a pulse or train of active stimulation) and recording the response to that perturbation in one or more brain regions (e.g., a stimulation-evoked potential). "Connectivity" may also include the application of a linear or non-linear transformation (e.g., a graph theoretical metric) to raw values computed from those operators. Those transformations may be computed in part by machine learning or other automatic optimization algorithms.

Neurostimulation technologies like cortical and deep brain stimulation ("DBS") can be used to target dysfunctional brain circuits that cause neurological and neuropsychiatric symptoms. Neural signal oscillations are important to effective neurostimulation. For example, clinically effective DBS in psychiatric and movement disorders, can be associated with changes in neural signal power and in synchrony of neural oscillations between brain structures. Similarly, local field potential ("LFP") synchrony can be a fundamental mechanism for inter-regional or within-region communication. Indeed, mental disorders seem to arise less from dysfunction of any single brain region, than from communication failures between brain regions. However, while the neuroscience community has repeatedly called for a broader focus on networks, conventional platforms cannot effectively measure network function, in part because they are overly optimized to detect conditions that arise from focal brain lesions.

To control synchrony, e.g., by locking electrical stimulation of a "downstream" region to the phase of an "upstream" region, phase determination must be performed. Conventional implantable medical devices have not been able to determine such phase estimations as the complex number and trigonometric calculations utilized are computationally intensive and expensive. The present disclosure provides, as will be described herein, a system that can estimate phase-related quantities (e.g., signal magnitude and phase, phase-locking value, phase-amplitude coupling) in real time. In addition, the system can estimate phase-related quantities from 64 neural channels, or more. Providing such a system in an implant imparts limitations on power, and the system described herein can estimate phase-related quantities within an implant-feasible power budget.

There are several candidate methods for phase extraction in hardware, with trade-offs in terms of power, silicon area, accuracy, and latency. A hardware implementation can use field-programmable gate arrays ("FPGA"), which are far outside the power budget and size of an implantable system. A discrete distance approximation ("DDA") can be used to estimate synchrony without trigonometric functions, but it cannot accurately compute phase for stimulation. Similarly, a coordinate rotation digital computer ("CORDIC") processor can be used to estimate synchrony, but it requires iterative shift-and-add operations with multi-stage pipelining and many clock cycles, increasing system latency in a way that prevents effective phase-locked stimulation.

Systems and methods according to various embodiments of the present technology may combine signal conditioning, digitization, and filtering, with phase extraction. The proposed systems and methods described herein can measure phase related metrics and control neural oscillation synchrony between subsets of neural channels, and is scalable to high-channel-count architectures (64 channels or more).

FIG. 1 is a block diagram of an exemplary stimulation system 100 in accordance with an embodiment. As shown, the stimulation system may generally include a stimulation assembly 102 and a controller 104 in communication with the stimulation assembly 102. The stimulation assembly 102 may include a number of stimulators 106 configured to monitor and deliver stimulations to record and control brain activity in the subject. The stimulators 106 may include deep brain stimulation electrodes. For example, the stimulators 106 can include multiple intracranial leads tunneled and connected to a cranial, sub-clavicular implant site. The stimulation assembly 102, or stimulators 106 therein, may be wholly or partially implanted in a patient's skull, scalp, or both, or the entire system 100 may be non-invasive and placed near or on the patient's body. The stimulation system may encompass a wide range of modes of energy delivery, including but not limited to, optical, electrical, magnetic, sonic, and thermal energy.

The stimulators 106 can include one or more cortical leads and one or more subcortical leads. According to one non-limiting example, the stimulators 106 can include three cortical leads and three subcortical leads. The stimulators 106 can include an electrode array sufficient for stimulation and sensing. According to one non-limiting example, a cortical array can include a 1×4 or 2×4 actuator array and a subcortical lead can include a 1×4 or a 1×8 actuator array. According to another non-limiting example, a cortical array can include a 1×4 or 2×4 actuator array and a subcortical array can include two segmented subcortical leads (e.g., in a 1-3-3-1 or a 3×4 configuration). The actuator array on the stimulators 106 can define a spacing between electrodes of between about 0.5 mm and about 2 mm. The actuator array on the stimulators 106 can define an actuator length of between about 0.5 mm and about 3 mm. The lead of the stimulators 106 can define a length of at least 40 cm. The lead of the stimulators 106 can define a diameter between about 0.1 mm to 2 mm. In a particularly preferred embodiment, the lead of the stimulators 106 can define a diameter of between about 1.2 mm and about 1.3 mm.

The controller 104 may generally include a processor 108, a memory 110, such as flash or other type of memory, a communication module 112, signal generation/signal detection modules 114, a real-time clock 116, and optionally a power source (not shown). According to some implementations, the controller 104 can include a signal processing application specific integrated circuit 1100 ("ASIC", see FIG. 11), which will be described in detail herein. The ASIC 1100 can be configured to control the brain sensing (e.g., monitoring) and brain stimulation algorithms described herein. As shown, the controller 104 may also include various connections, or terminals 118 for transmitting signals generated by the signal generation module 114. Any or all of these elements may be implanted into a patient's body or carried/worn externally to the body, or some elements may be used in each configuration with an appropriate interconnection system. According to some implementations, the controller 104 can be included within the stimulation assembly 102. According to other implementations, the controller 104 can be remote from the stimulation assembly 102.

In some implementations, the controller 104 may also include, or be in communication with, a graphical user interface ("GUI") 105 including an input 107 for accepting user selections, operational instructions and information, as well as an output 109 or display for providing a report or displaying recorded data. The GUI 105 can be configured as a laptop, tablet, or computer, among others. The input 107 may include various user interface elements, such as a mouse, keyboard, touchpad, touch screen, buttons, and the like. The input 107 may also include various drives and receptacles, such as flash-drives, USB drives, CD/DVD drives, and other computer-readable medium receptacles, for receiving various data and information. To this end, the input 107 may also include various communication ports and modules (e.g., communication module 112), such as Ethernet, Bluetooth, or WiFi, for exchanging data and information with various external computers, systems, devices, machines, mainframes, servers or networks. The GUI 105 can provide the ability to configure sensing and triggering functions of the system 100.

The processor 108 may be configured or programmed to perform a variety of functions for operating the controller 104 using instructions stored in memory 110, in the form of a non-transitory computer readable medium, or instructions received via input. In some implementations, the processor 108 may control the sending and receiving of instructions and operational parameters (for example, via a wireless transcutaneous link in the communication module 112), the storage of the operational or stimulation parameters and instructions in memory 110, the transmission of the operational parameters to signal generators in the signal generation module 114, the selective triggering of the signal generators to provide electrical, and other types of stimulations, to various brain regions or tissues of a subject, as well as synchronizing various functions using the real-time clock 116. By way of example, the processor 108 can be a programmable microprocessor, microcomputer, or application specific analog and/or digital integrated circuits and/or hardware and software modules. For instance, the controller 104 may communicate with the real-time clock 116 to determine the timing, phase or phase lag, and synchronization of various stimulations. The controller 104 may also communicate with the real-time clock 116, as well as other hardware and digital logic circuitry, to accurately store activation times in memory 110 and provide activation counts. The system 100 can generate a clock signal from the real-time clock 116 for onboard components including the controller 104 and the processor 108, which can provide tracking of wall time/date to identify the timing of relevant clinical events. The controller 104 can also re-synchronize that clock to an external source (e.g., to the clinician programmer).

The signal generation module 114, in communication with the processor 108, may include a number of signal generators for providing activating signals to the stimulators 106. In some implementations, each of the stimulators 106 may be individually controlled using separate signal generators. The signal generators can be independently operated, either sequentially or concomitantly, by the processor 108, to provide stimulation signals with various intensities, frequencies, phases, pulse widths, durations and waveforms. In one embodiment, the signal generators may be controlled to provide stimulations in accordance with the methods described below with respect to FIGS. 2-4. In addition, in some implementations, the signal generation module 114 may include an output sensing circuit to monitor contact output, as well as other fail-safe mechanisms.

The signal detection module 114 may include various hardware, and be configured to detect brain signals acquired using the stimulation assembly 102. For instance, the signal detection module 114 can include various analog-to-digital converters, voltage/current meters, amplifiers, filters, and other elements. Signals from the signal detection module 114 may then be provided as input and processed by the processor 108. Alternatively, the signals may be stored in the memory 110 and subsequently accessed/processed by the processor 108. As will be described in detail herein, the signal generation/detection module 114, processor 108, and other aspects of the controller 104 can be configured as, included on, or in communication with, an application-specific integrated circuit ("ASIC") for execution of the methods described herein or for use with the system 100 described herein.

In some aspects, the processor 108 may receive signals corresponding to brain activity in one or more regions of a subject's brain as input from the stimulation assembly 102 received through the signal detection module 114. The processor 108 may then analyze the signals, for example, to determine a connectivity between two or more brain regions being monitored by the stimulation assembly 102, for example, by computing various metrics indicative of connectivity, such as coherence, evoked potentials, and others or to determine (or detect) a phase of oscillation of one or more brain regions. In some aspects, the processor 108 may receive such information from various input elements configured on the controller 104, as described, or alternatively from an external or remote device, computer or system, by way of the communication module 112 (e.g., an EEG). The processor 108 may also access a reference or database, as described, stored locally in the memory 110, or at storage location. As will be described herein, the controller 104 may operate in a closed-loop fashion to control brain activity in a subject by operating or instructing the signal generation module 114 to provide targeted stimulations in response to measured connectivity levels between two or more regions of a subject's brain, or in response to specific activity in one or more regions of a subject's brain.

In some implementations, the controller 104, along with the stimulation assembly 102, may be part of a standalone stimulation system. Alternatively, the controller 104 may be a wearable or implantable unit (e.g., a rechargeable implantable neurostimulator, "INS") that is programmable or configurable using an external device, computer or system. To this end, the communication module 112 may be configured to send and receive various signals, as well as receive power. Specifically, the communication module 112 may include an antenna, or an input-output wire coil, a receiver and transmitter, data converters, as well as other hardware components. As a non-limiting example, the receiver and transmitter may be configured to receive and transmit radio-frequency (RF) signals. In some implementations, the antenna may be configured for transcutaneous wireless two-way communication with an external wearable device, sending and receiving signals when the external wearable device is placed in close proximity. The communication signals may be transmitted through magnetic induction and include information for operating and/or programming the processor 108. For instance, the communication signals may include triggers or command signals for generating stimulations. In some aspects, transmitted signals may also be configured to power or recharge battery components powering the controller 104. The antenna may be connected to a receiver and transmitter, which in turn may be connected to serial-to-parallel and parallel-to-serial data convertors, respectively. Any information sent or received, as described, may then be processed by the processor 108.

The INS can include four contacts on each of the four leads, and in some implementations, eight contacts on each of the four leads. The leads can define a lead contact impedance of under 5 kOhm, and in some cases, under 2 kOhm. According to one non-limiting example, the INS includes two current sources per header, and in some cases, 32 current sources in total. According to one non-limiting example, the INS includes four recording channels per header, and in some cases, 32 recording channels in total. The INS can be configured to provide a stimulation amplitude between 0 and 8 mA, and in some cases, 0 to 25 mA. The INS can be configured to provide a stimulation frequency between 0 and 200 Hz, and in some cases, 0 to 10,000 Hz. As will be described, the INS (e.g., stimulators 106) can be configured to provide stimulation triggered upon a user-defined signal phase, and in some cases, provide stimulation triggered randomly relative to a detected event (e.g., a connectivity level being out of range).

The INS can be configured to provide a stimulation pulse width between 50 and 500 μs, and in some cases, 30 to 1000 μs. The INS can be configured to provide a stimulation waveform with a variety of patterns. Examples may include square, sinusoidal, or a sawtooth pattern. The INS can be configured to provide a stimulation in a response time within 250 μs, and in some cases, within 50 μs. The INS can be configured to provide stimulation capable of randomizing the delay between an event/trigger and stimulation onset. In some cases the delay is between 1 and 100 ms, in some cases between 1 and 1000 ms, in a uniform or non-uniform distribution. The INS can be configured to provide real-time data streaming of, for example, eight channels of data at 1 kHz, and in some cases, up to 64 channels of data.

As mentioned, the controller 104 may be powered by an internal and/or external power source. For example, an internal source may include a standard rechargeable battery, comparable to batteries used in implantable devices (e.g., pacemakers). Alternatively, or additionally, the internal power source may include a capacitor in combination with a regulator, such as a single ended primary inductor converter or dc-dc converter, that together can generate a constant current or voltage output for short periods of time. In some implementations, the capacitor may be charged by an external wearable device. As such, the controller 104 may include an induction coil, or thin, tightly wound wire that allows for RF telemetry and/or battery recharge by an external wearable device, configured either as part of the communication module 112, or as separate hardware. Other methods of charging, such as ultrasonic power transfer, may also be utilized.

Figure 2:
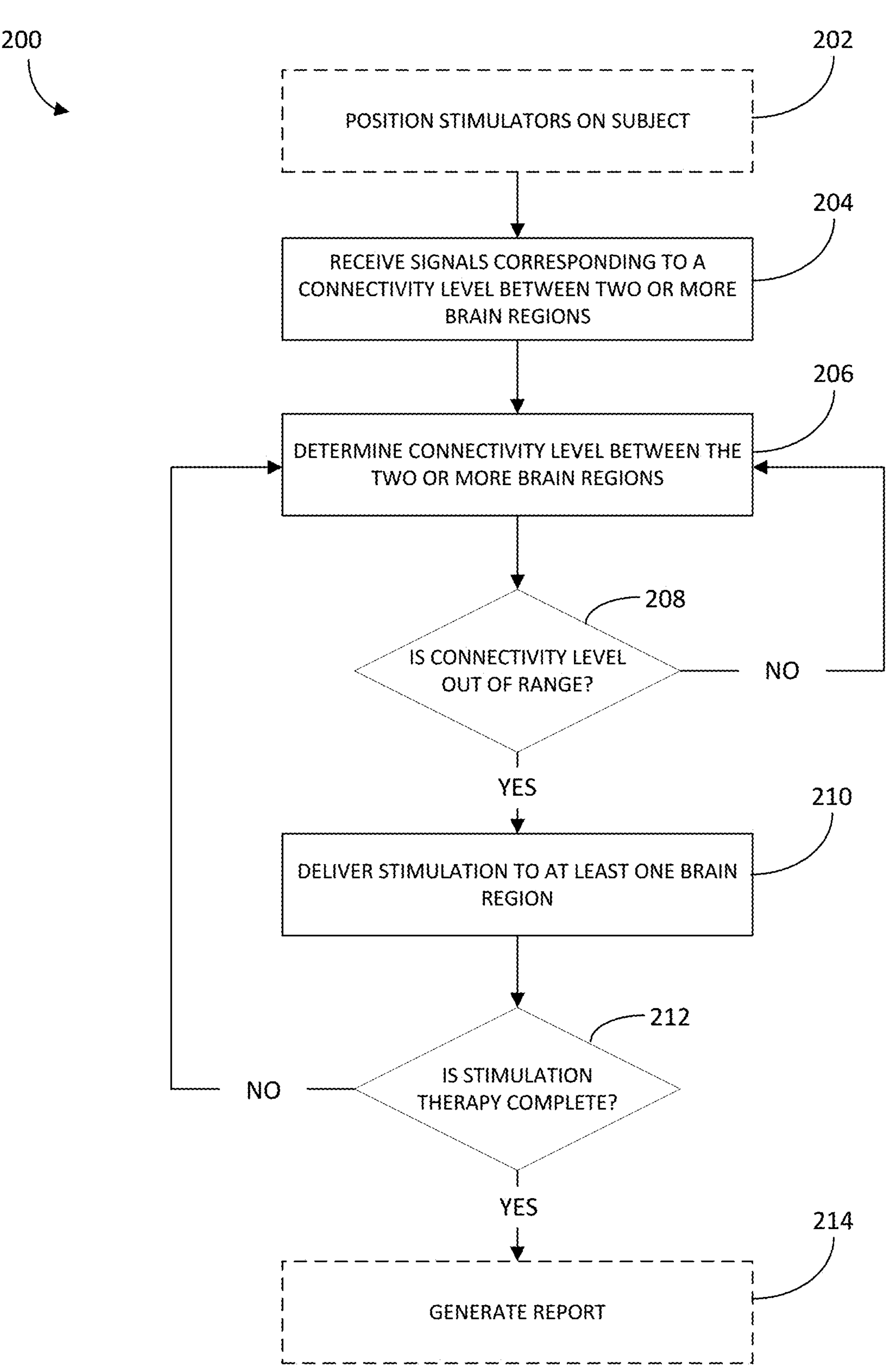
FIG. 2 illustrates a method for restoring brain activity in accordance with a first embodiment.

FIG. 2 illustrates a method for controlling connectivity levels 200 in a plurality of brain regions by providing targeted stimulations in accordance with an embodiment. The method may be carried out using any suitable device, apparatus or system, such as the stimulation system 100 described above with respect to FIG. 1. In some embodiments, the method may be implemented as a program, software or instructions stored in a memory such as a non-transitory computer readable medium or other storage location, that are executable, at least in part, by the processor 108.

At block 202, the method may optionally begin with positioning stimulators (e.g., implanting DBS stimulators, positioning non-invasive transducers) to stimulate a subject's brain. In an embodiment, a number of stimulators (e.g., stimulators 106 shown in FIG. 1) may be positioned to stimulate more than one target region of the subject's brain. For example, the stimulators may be positions to stimulate two or more target regions. For example, a first stimulator 106 can be placed at a first target region and a second stimulator 106 can be placed at a second target region, and so on (including third, fourth, and fifth target regions, etc.). The first and second target regions may be separate regions of the brain and may or may not spatially overlap. However, positioning or implantation need not be carried out during execution of the process, but rather during a prior procedure or intervention.

At block 204, signals corresponding to connectivity between the first and second target regions of the subject's brain are received, for example, by the signal detection module 114 of the controller 104 (shown in FIG. 1). As noted above, the signals may be spontaneous or may be evoked by delivery of any modality of stimulus, including visual/auditory or other sensory stimuli. According to one non-limiting example, the signals can be LFP within at least one predetermined frequency band. The received signals can be sent to the processor 108. At block 206, the received signals are measured and calculated by the processor 108 to determine a connectivity level between the first and second target regions. For example, the phase of the signals from the first and second target regions can be determined and the connectivity level can be a calculated phase-locking value ("PLV") between the first and second target regions for the brain. According to another non-limiting example, the connectivity level is a phase-amplitude coupling value determined from the phase of the received signals from the first target region and the amplitude or power of the received signals from the second target region. At block 208, the measured connectivity level can be compared to a predetermined desired therapeutic range. For example, the measured connectivity level can be a dimensionless parameter between 0 and 1. The dimensionless parameter can be based on a normalization of sensed signals to a prior baseline, to phase-amplitude coupling, coherence, or phase-locking value. According to some implementations, the predetermined therapeutic range can be subject specific and/or be determined and input by a clinician performing the stimulation.

If the measured connectivity level is within the predetermined therapeutic range, the method returns to block 206 to continue measurement and calculation of the connectivity level between the first and second target regions (e.g., without providing stimulation). According to some embodiments, there may be a period of delay between measurements, which may range anywhere from 1 millisecond to many hours. For instance, the therapy may be configured to sample in duty cycles of 1 minute out of every 10-60 minutes, or of 10 minutes out of every 60-300 minutes. If the measured connectivity level is outside the predetermined therapeutic range, the method proceeds to block 210 to deliver a stimulation to one or more of the first and second target regions of a subject's brain. That is, the system remains in a sense/record/monitor mode (e.g., for approximately 90% of a treatment, or more), and transitions into a stimulation mode upon the determination of an event that requires stimulation. For example, determining that a measured connectivity level is out of a predetermined range and has remained so for an adequate duration of time. In that way, the method provides responsive stimulation that is based on connectivity levels between brain regions.

Figure 5:
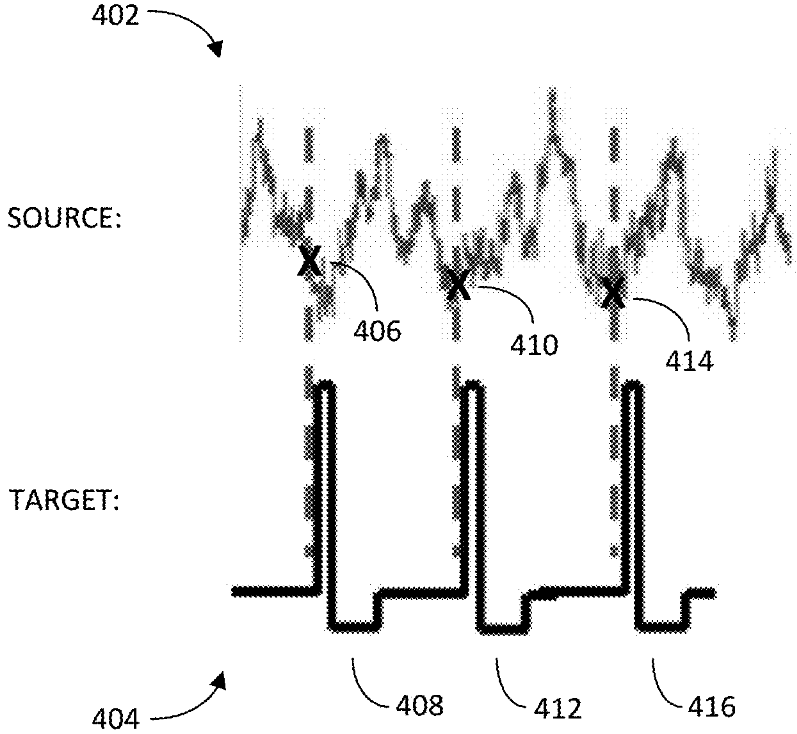
FIG. 5 illustrates phase-timed stimulation to stimulate a brain region at a particular phase of a neurological signal.
Figure 6A:
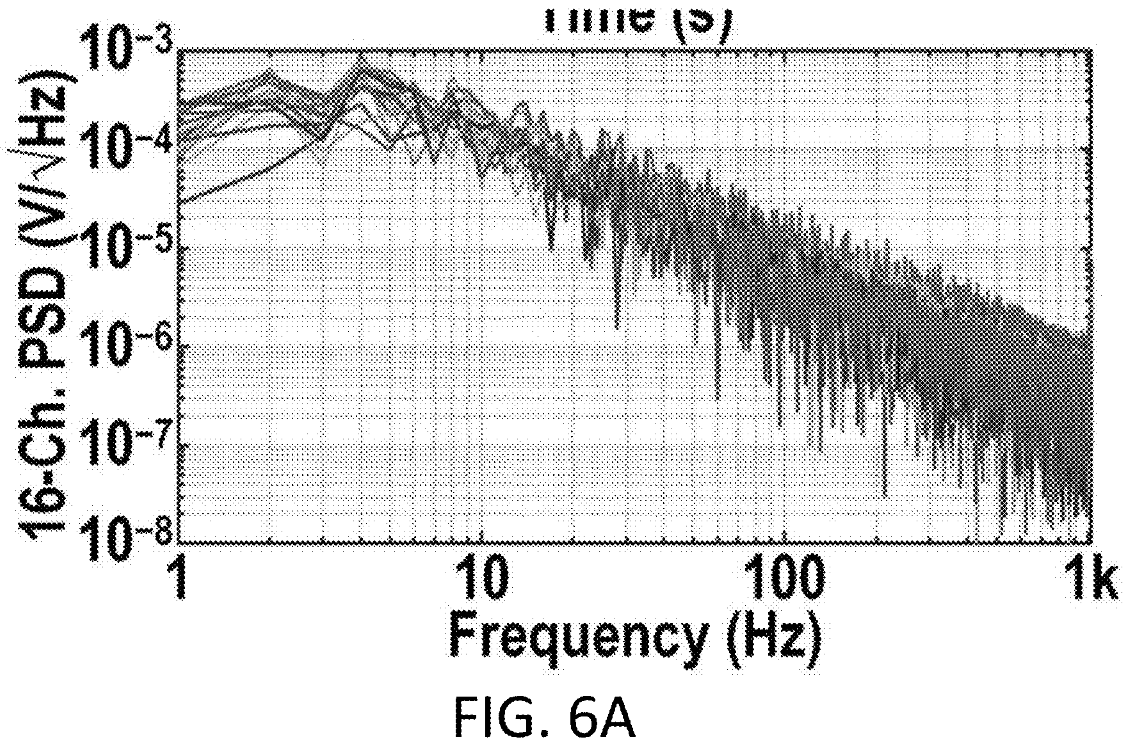
FIG. 6A illustrates the PSD of 16-channel input-referred local field potential ("LFP").
Figure 6B:
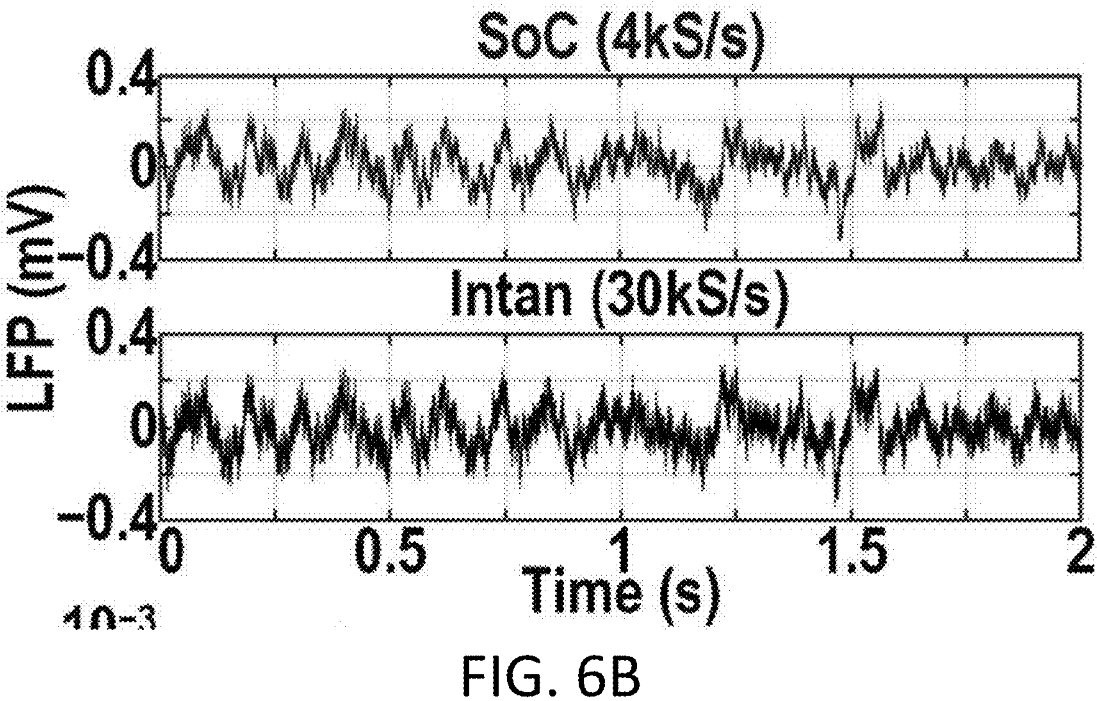
FIG. 6B illustrates LFP measurements in the application of the systems and methods described herein.
Figure 6C:
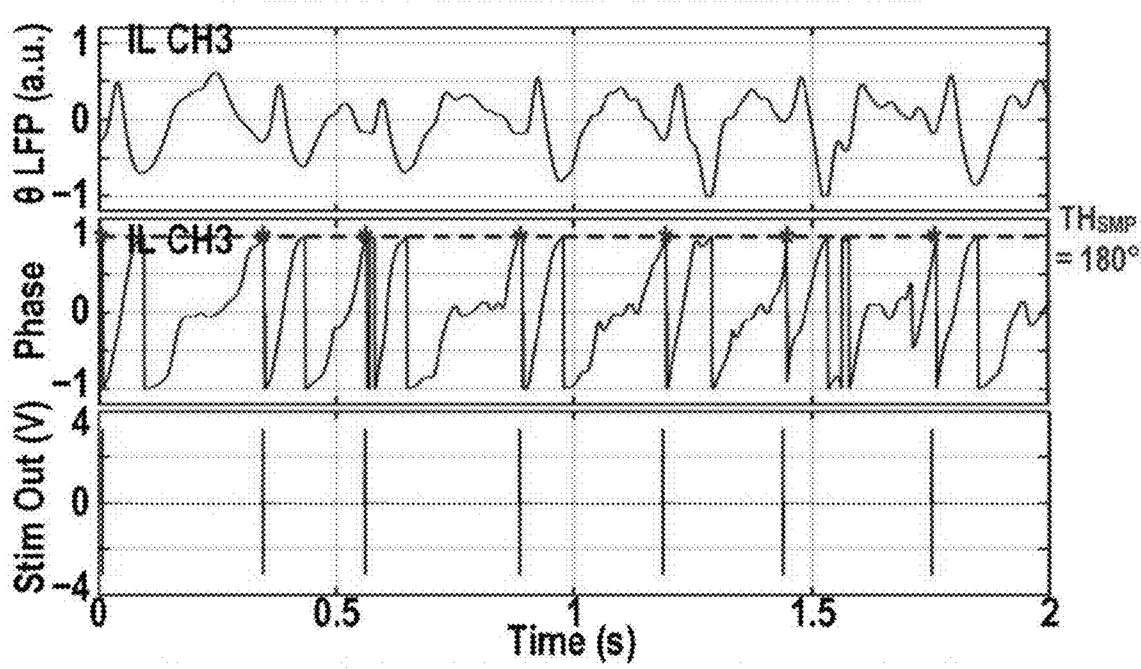
FIG. 6C illustrates the extraction of phase from a signal and the time-locked stimulation of a brain to that extracted phase in accordance with the systems and methods described herein.

According to some implementations, the stimulations may be time-locked to the phase of an oscillation in one or more of the first or second target region (see, e.g., FIGS. 5 and 6C). For example, the stimulation may be delivered using the stimulators 106 as shown in FIG. 1. According to some implementations, a response time (e.g., delay) of the stimulation relative to the determination that the measured connectivity level is outside the predetermined therapeutic range can be between about 50 μs and about 250 s. It may frequently be advantageous for this delay to be in the range of 1 to 100 ms, to leverage timing dependent plasticity principles. In other implementations, the stimulation may be time-locked to a change in amplitude of an oscillation in one or more brain regions (e.g., from the first or second target region), or to a rise in voltage that signifies a change in tissue excitability. Oscillatory phase, amplitude, or any combination of these may be weighted and combined between one or more regions to determine stimulation. In a non-limiting example, the amplitude and phase of a region may both be tracked. For example, stimulation may be delivered at a target oscillatory phase (e.g., 180 degrees), but only when the amplitude/power of the same oscillation is above a predetermined amplitude/power threshold. The specific oscillatory phase to be targeted may be selected by a clinician on the basis of specific properties or observed responses of the measured brain structures. This may include the response to test stimulations. For example, the controller 104 can detect the phase of a signal, however if the amplitude of that signal is below a predetermined amplitude threshold, stimulation will not be delivered. This can ensure that the phase detection is of high quality. In some examples, this timing may change after each detection event, e.g. being randomized according to a pre-specified distribution. For example, the stimulation may be delivered at a target oscillatory phase, where that target phase is randomized from one stimulation to the next. That is, a stimulation pulse can be delivered at a phase that is randomized and different from the target phase of a previously delivered stimulation pulse.

According to other implementations, the stimulations may be time-locked to a change in activity level of one or more brain regions. For example, the stimulation may be time locked to a change in the overall activity level of one or more regions of the brain. This activity level may be represented as a change in an oscillation, as in the prior examples, or may reflect an alternate measure of neural activity such as a voltage or other physical signal produced by the brain. The desired activity level may be an increase or decrease beyond a user-specified threshold, and there may optionally be a requirement that the increase or decrease persist for a user-specified amount of time. Upon detection of this change in activity, stimulation may be delivered to one or more brain regions with timing relative to the change. The timing or delay between detection and stimulation can be between about 50 μs and about 250 s. It may frequently be advantageous for this delay to be in the range of 1 to 100 ms, to leverage timing dependent plasticity principles. In some examples, the timing of stimulation may change after each detection event, e.g. being randomized according to a pre-specified distribution.

In an embodiment, a stimulation may be delivered to one or more of the first and second target regions. For example, a stimulation may be delivered to a first target region and a second target region. The stimulation (e.g., electrical or other modality of stimulation) may be monophasic or biphasic, with the stimulation having any waveform or shape. The stimulation may be a single pulse, trains of pulses, continuous, or intermittent in the form of current or voltages, light, and so on, having various amplitudes, frequencies, periods, waveforms, durations, phases, polarities, and so on. For example, a stimulation pulse or train of pulses may be delivered to one or more target regions. Specifically, a first pulse or train of pulses can be delivered to the first region and a second pulse or train of pulses can be delivered to the second region. The stimulation pulse can define a pulse width between about 30 μs and about 50,000 μs. In other examples, the pulse widths can be in the range of 50 μs to 250 μs in applications involving electrical stimulation, or of 10-20 ms (10,000-20,000 μs) in applications involving light stimulation. According to some implementations, a patterned stimulation can be delivered to one or more brain areas, for example, a paired pulse or paired pulse train. For example, a first pulse (or train) can be delivered to a first region and a second pulse (or train) can be simultaneously delivered to a second region, thereby pairing the first and second pulses. The timing between pulses within a train and/or between pulses of different trains may be controlled in a precise fashion to achieve a desired response.

According to some implementations, the stimulation period can be between about 0.1 seconds to about 1,000 seconds. It may be particularly advantageous for brief stimulation periods to correspond to the measurement period of an oscillation of interest, in the range of 0.5 to 5 ms. It may similarly be advantageous for stimulation periods to be below the limit of human detection, constrained to 5 seconds or less. According to some implementations, the stimulation amplitude may be between about 0 and about 25 mA. In some implementations, the stimulation frequency can be between about 1 Hz to about 10,000 Hz. In one embodiment, a user may select pre-programmed stimulation parameters such as target frequencies, intensities, durations, timings, and so on. Other information may be taken into consideration when setting the parameters of the stimulation such as a condition or disorder of the subject, targeted structures or regions in the brain, and properties (e.g., electrical, optical, magnetic) of such regions. In an embodiment, a user may also provide selections indicative of such targeted regions, tissue properties, subject disorder or conditions, and so on. In one such example, the stimulation frequencies may be chosen to match a target oscillation present within the targeted tissue. For instance, frequencies of the beta frequency band (15-30 Hz) may be targeted for disorders involving movement, whereas frequencies of the theta (5-8 Hz) and alpha (8-15 Hz) bands may be targeted for disorders involving long range communication in cognitive circuits.

The stimulation may be part of a stimulation sequence designed to provide more than one stimulation (e.g., pulse, paired pulse, pulse train, or paired pulse train) over a selected or determined period of time. In an embodiment, the predetermined phase for the source region used to trigger delivery of a stimulation pulse to the target region is the same phase value or the same phase range for each stimulation pulse in the stimulation sequence. In another embodiment, the predetermined phase or predetermined phase range used to trigger delivery of a stimulation pulse to the target region may change or vary for each stimulation pulse. In another embodiment, the timing in seconds rather than the phase angle may be controlled and/or varied.

With continued reference to FIG. 2, if the stimulation therapy is not complete at block 212, the process returns to block 206. If the measured connectivity level is not within the predetermined therapeutic range at block 208, the stimulation continues (block 210) until the connectivity level is within the predetermined therapeutic range. The number of loops between steps 206 and 212 that are executed (e.g., by the system 100 of FIG. 1) can be predetermined or set by a clinician, and can be considered the "dosing" of the stimulation therapy. For example, the stimulation therapy can be set to execute between 1 and 200 loops of the method 200. As illustrated, the sensing and stimulation is closed-loop, whereby the stimulation is based on, and triggered, by a measured parameter (e.g., phase, PLV, amplitude, etc.).

Returning to FIG. 2, if the stimulation therapy is complete at block 212, a report may optionally be generated and displayed (e.g., by the GUI 105 of FIG. 1) at block 214. The report may be in any form and include any information including any stimulations, parameters thereof, or measurements acquired from a subject. In some aspects, the report may include the selected stimulation sequence in the form of instructions, executable by a stimulation system. The report may include measurements such as, for example, local field potential (LFP) measurements, electroencephalogram (EEG) measurements, single-neuron measurements, multi-neuron measurements, spike measurements, optical measurements, sonic measurements and others. The report may also include various metrics of connectivity that may be generated based on one or more such measurements. The metrics of connectivity may include evoked potentials or oscillations, coherence, cross-correlations, multi-signal computations, principal-component computations, and so on. In one aspect, coherence between regions of the brain may be computed using respective LFP signals, which may then be used to determine a connectivity or a connectivity between the regions. The metrics of connectivity may be used to select parameters for further application of the methods for stimulation described herein.

Figure 3:
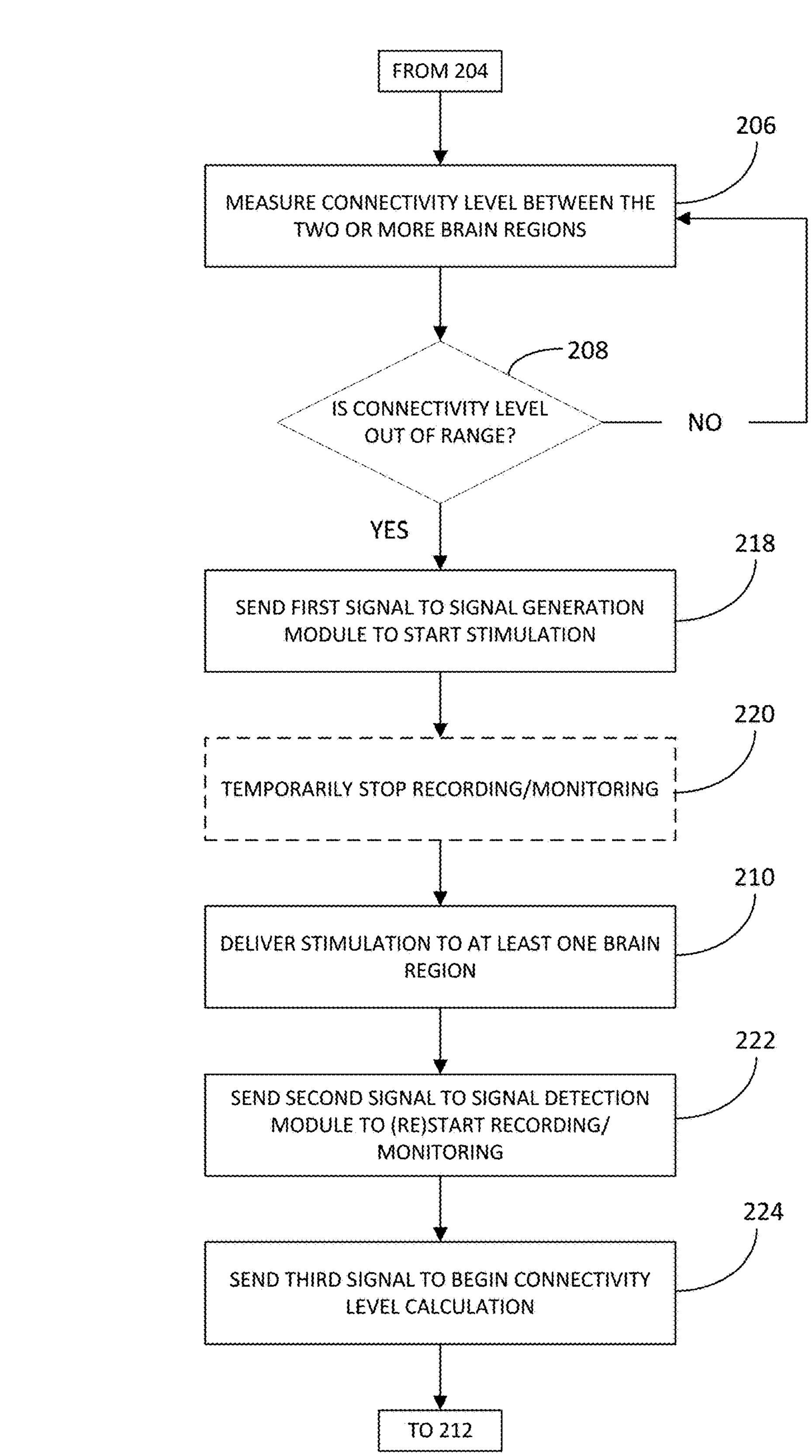
FIG. 3 illustrates a method for restoring brain activity in accordance with a second embodiment.

FIG. 3 illustrates an optional or alternative configuration for the method 200 for controlling connectivity levels of FIG. 2. In the illustrated method, like reference numerals correspond to previously described blocks of method 200. For example, at block 208, the measured connectivity level can be compared to a predetermined desired therapeutic range. If the measured connectivity level is within the predetermined therapeutic range, the method returns to block 206 to continue measurement and calculation of the connectivity level between the first and second target regions. If the measured connectivity level is outside the predetermined therapeutic range, the method 200 can proceed to block 218 where the processor 108 sends a first signal (e.g., an "enable stim" signal or "$EN_{STIM}$" signal) to the signal generation module 114 to command the signal generation module 114 to start the delivery of stimulation. According to one implementation, the first signal is sent between 1 μs to 50 ms of the determination connectivity level is outside the predetermined therapeutic range. Optionally, at block 220, the processor 108 can simultaneously send a signal to the signal detection module 114 to command the signal detection module 114 to temporarily stop or pause the recording or monitoring of brain signals. According to one implementation, the recording is paused within 1 ms of the determination that connectivity level is outside the predetermined therapeutic range. This can, for example, protect sensitive sensing circuitry to be protected and inoperable during high-energy stimulation.

The method 200 can then proceed to block 210 to deliver a stimulation to one or more target regions of a subject's brain. At block 222, the processor 108 can send a second signal (e.g., a "high" signal) to the signal detection module 114 to command the signal detection module 114 to restart the recording of brain signals. According to one implementation, the second signal is sent within 10 ms of the completion of the stimulation. According to one implementation, the recording of brain signals resumes within 1 ms of receiving the second signal. Next, at block 224, the processor 108 can send a third signal (e.g., a "low" signal) to the signal detection module 114 to begin monitoring/calculating the connectivity level between the first and second target regions. According to some implementations, a predetermined delay between the second signal and the third signal is implemented. The predetermined delay can be application-specific. According to one implementation, the monitoring of the connectivity levels begins within 100 ms of receiving the third signal. The method 200 can then proceed to block 212 and proceed with the method 200 previously described with respect to FIG. 2.

Figure 4:
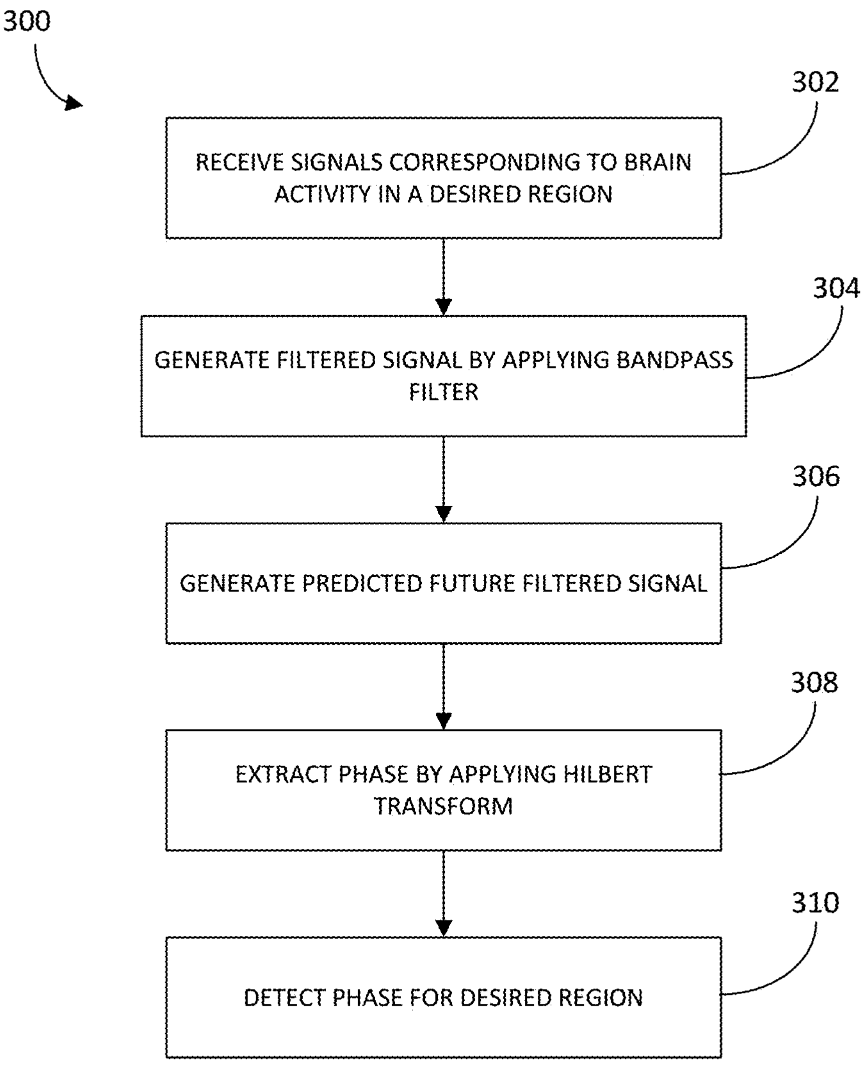
FIG. 4 illustrates a method of detecting a phase of oscillation of a neurological signal from a region of a subject's brain.

FIG. 4 illustrates an exemplary method for determining the phase of oscillations in a target region in accordance with an embodiment. The method can be executed by the controller 104 of the system 100 of FIG. 1 previously described (e.g., by the ASIC 1100 described herein with respect to FIG. 11). The determined phase of oscillations may be used in order to provide stimulations that are time-locked to the phase of oscillations (e.g., providing stimulation at 180 degrees). The signal detection module 114 (see FIG. 1) can be used to determine (or detect) the phase of oscillations of a desired brain region in a predetermined frequency band. Various known methods may be used to detect the phase of oscillations such as, for example, sliding-window Fourier transforms, all-pass Hilbert filters or latent-variable or state-space tracking methods. In one embodiment, a continuous phase estimation method is used to determine the phase of the source signals and to minimize error from the desired region and variance in the stimulation phases.

Referring to FIG. 4, at block 302 signals corresponding to brain activity may be received from the desired region. At block 304, a bandpass filter is applied to the signals to generate filtered signals. At block 306, predicted future filtered signals are generated by using an autoregressive method on the filtered signals. At block 308, phase information is extracted from the filtered signals (including both the filtered signals and the predicted future filtered signals) by applying a Hilbert transform. In an embodiment, current samples from the filtered signals are centered to minimize edge distortion. At block 310, the extracted phase information is used to detect the phase of oscillations for the current samples or time points for the desired region. In an embodiment, the method may output a phase for each input sample ("continuously"), thereby reducing stimulation delay.

FIG. 5 illustrates timing of stimulation pulses in a target region (e.g., one or both of the first and second target regions) based on a phase of oscillation in from a desired brain region (e.g., a separate "source" region, or one of the first or second target regions) in accordance with an embodiment. The phase can be extracted utilizing, for example, the method described with respect to FIG. 4 or with the ASIC 1100 described herein with respect to FIG. 11. In FIG. 5, the predetermined phase (e.g., about 180 degrees) or the predetermined phase range (e.g., between 0 and 360 degrees) is used to trigger a stimulation pulse for a target region is the same for each stimulation pulse in a stimulation sequence 404. This may be selected on an individual basis for a patient and brain area, for example by computing a phase response curve and identifying a phase at which the effects of stimulation are optimal. In one specific and non-limiting example, the phase of source signals 402 for a source region may be monitored in a specific frequency band (e.g., the theta band 4-8 Hz) to determine when the phase of the source signal is at or near 180°. When the phase of oscillation is equal to or near 180° at a first predetermined phase occurrence 406, a first stimulation pulse 408 is delivered to the target region. A second predetermined phase occurrence 410 triggers delivery of a second stimulation pulse 412 to the target region and a third predetermined phase occurrence 414 triggers delivery of a third stimulation pulse 416 to the target region. As discussed above, the stimulation sequence 404 affects the connectivity level between two or more brain regions, and the stimulation can be repeated until the connectivity level is restored to be within a predetermined therapeutic range. This similar example could generalize to a wide range of other frequencies, for instance to delta (1-4 Hz), alpha (8-15 Hz), beta (15-30 Hz), gamma (30-50 Hz), broadband gamma (50-200+Hz), or spindle (~200 Hz) oscillations. According to some examples, the frequency bands can be in the range of 5-15 Hz, 15-30 Hz, and 30-200 Hz.

FIGS. 6A-6D illustrates one specific non-limiting implementation of the systems and methods previously described herein utilized on a rodent model (Long-Evans rats), as executed by the ASIC 1100 described below with respect to FIG. 11 integrated into the system 100 described above. FIGS. 6A-6D demonstrates 16-channel LFP recording and phase-locked stimulation operating in two modes: a first mode where stimulation is delivered at a target oscillatory phase (e.g., 180 degrees), and a second mode where stimulation is delivered at a target oscillatory phase if the connectivity level (e.g., PLV) between first and second regions of the brain is outside a predetermined therapeutic range. In the illustrated non-limiting examples of FIGS. 6A-6D, two custom electrode arrays (8 recording and 2 stimulation channels in each) were implanted into the infralimbic cortex (IL) and basolateral amygdala (BLA). The power spectral density "PSD" of 16-channel input-referred LFP exhibits prominent 1/f-shaped spectrum (see FIG. 6A). Simultaneous recording using the ASIC 1100 (e.g., "Sort") described below integrated into the system 100 described above compared to recording using a commercial device (Intan 32-ch headstage #C3314) verifies accurate measurement of LFP activity (see FIG. 6B). To demonstrate the phase-locked stimulation capabilities of the system 100, and the ASIC 1100 described herein, the system was operated in the first mode (see FIG. 6C) and stimulation was targeted at a specific phase (e.g., 180°) of a predetermined frequency band LFP (e.g., theta band, 4-8 Hz). In this illustrated non-limiting example, the theta band LFP is known to correlate with fear- and anxiety-like behavior. The system was then operated in the second mode (see FIG. 6D), where theta-band phase- and PLV-locked stimulation was further demonstrated. For both non-limiting examples, the maximum stimulation frequency was set to 6 Hz, and the phase-locking detector was controlled such that phase wrapping did not trigger the stimulation.

As illustrated in FIG. 6C, theta band LFP can be monitored in one or both of a first or second target region by the stimulation detection module 114 of the system 100. The controller 104 (e.g., the ASIC 1100 described below) can extract the phase from the signal. The controller 104 can then determine the points at which the phase of oscillation of the signal is at a predetermined phase, in this example, 180 degrees. The controller 104 can then command the stimulation generation module 114 to apply a stimulation to one or both of the first or second target region that is time-locked to the predetermined phase.

As illustrated in FIG. 6D, theta band LFP can be monitored in one or both of a first or second target region by the stimulation detection module 114 of the system 100. The controller 104 (e.g., the ASIC 1100 described below) can extract the phase from the signal. The controller 104 can then determine the points at which the phase of oscillation of the signal is at a predetermined phase, in this example, 180 degrees. The controller 104 can then calculate the PLV in the phase signals between the first and second target regions and determine if the PLV is outside of a predetermined therapeutic range. In this example, the therapeutic range is between 0 and 0.5. If the PLV is outside the therapeutic range (e.g., greater than 0.5), the controller 104 can then command the stimulation generation module 114 to apply a stimulation to one or both of the first or second target region that is time-locked to the predetermined phase only if the PLV is outside the therapeutic range. As illustrated in FIG. 6D, this targeted, responsive stimulation elicits a reduction in the connectivity level between the first and second target regions, as shown by a reduction in PLV post-stimulation.

According to another implementation, a method for determining an increase or decrease in connectivity, and tying that increase or decrease with targeted stimulation is provided. For example, abnormal connectivity (e.g., PLV) can be measured between two or more regions of a subject's brain (e.g., signal generation/signal detection modules 114). A change (i.e., increase or decrease) in connectivity can then be detected in a first brain region of the subject's brain. The stimulators 106 (FIG. 1), using the signal generation module 114, can then deliver stimulation to the first brain region. According to some implementations, the brain stimulation can be delivered relative to an increase or decrease in the detected connectivity level. The method may then repeat the detection and stimulation delivery steps a predetermined number of times. The method may then proceed with continued measurements of the abnormal connectivity until the connectivity has normalized.

As described above, aspects of the controller 104 of the system 100 can be integrated into an application-specific integrated circuit ("ASIC"), which can facilitate accurate, low-power phase extraction that implements low-power hardware-efficient algorithms for complex-number calculations. An ASIC according to various embodiments can define a chip of less than 1 $mm^2$ area and require a supply voltage of about 0.8 V. The proposed application-specific integrated circuit can also define a power consumption of less than 100 μW. This application-specific integrated circuit can be installed within a novel stimulation implant (e.g., an INS), with a similar form factor to a DBS. Such an implant with synchrony measurement and closed-loop stimulation capability can benefit many intractable brain disorders such as mental disorders, Parkinson's disease, and epilepsy. Importantly, previous efforts on open-loop DBS for mental disorders have not met the clinical needs, and systems and methods according to various aspects of the present technology can address this unmet need for treating disorders such as treatment-resistant depression, anxiety, and PTSD, among others.

According to one aspect of the present disclosure, a hardware-efficient method to estimate the instantaneous phase of neural oscillations is provided. This method overcomes the power-accuracy-latency drawbacks of the conventional methods noted above. As detailed below, this method may be based on a linear arctangent approximation ("LAA") algorithm to estimate the instantaneous phase of neural oscillations.

Linear Arctangent Approximation Algorithm

Figure 7A:
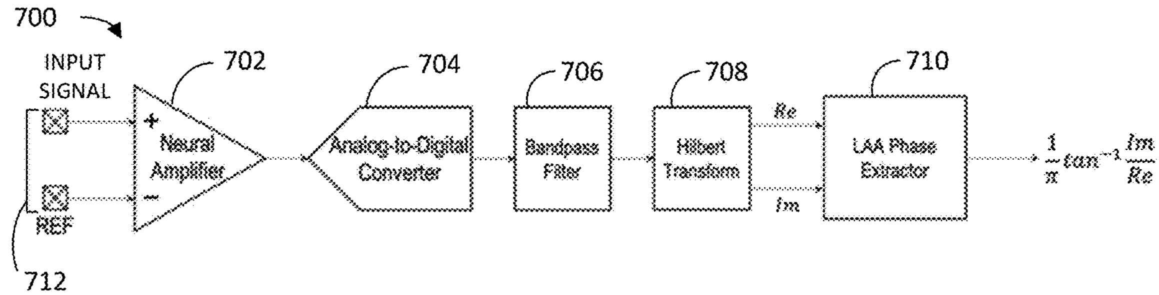
FIG. 7A depicts a schematic of a signal processing chain for phase extraction from an oscillating signal according to one aspect of the present disclosure.

FIG. 7A depicts a simplified block diagram of a signal processing chain 700 for determining (also referred to as "extracting") phase from an oscillating signal, such as a neural signal. The signal processing chain 700 may comprise any suitable system or method for conditioning the input signal and providing its phase. In some embodiments, a monopolar or bipolar signal, for example from a DBS lead, may be coupled with an amplifier 702. The output of the amplifier 702 may then be converted to a digital signal, for example by an analog-to-digital converter (ADC) 704, and may be filtered for one or more frequency ranges, for example by a bandpass filter 706. In some embodiments, the frequencies passed by the bandpass filter 706 may comprise one or more of Delta (δ, approximately 1-4 Hz), Theta (θ, approximately 4-8 Hz), Alpha (α, approximately 8-13 Hz), Beta (β, approximately 13-30 Hz), Low gamma (low γ, approximately 30-50 Hz), Gamma (γ, approximately 50-80 Hz), High gamma (high γ, approximately 80-150 Hz), Ripple (approximately 150-250 Hz), and Fast ripple (approximately 250-500 Hz) brain waves.

The bandpass filter 706 may comprise any suitable system or method for allowing signals with selected range(s) of frequencies to pass from input to output, while preventing unwanted frequencies from passing. The ADC 704 may comprise any suitable analog-to-digital converter and may be configured to output a digital signal of any suitable bit width for the signal processing chain 700. In some embodiments, a neural recording front-end requires at least 7 (in some embodiments, 8) effective number of bits to record neural signals (<1 mV LFP) in view of the background noise picked up by the electrodes (~10 uVrms). For amplifiers having non-linearity, a 9 to 10-bit ADC may be a suitable design choice to achieve 7 to 8 effective number of bits. The accuracy of phases and features measured increases marginally above 10 bits while the hardware complexity grows significantly. In some embodiments the ADC 704 may comprise a 10-bit ADC.

In some embodiments, the digitized and filtered oscillating signal may then be converted 708 into corresponding real and imaginary components from which phase may be extracted 710. The real ("Re") and imaginary ("/m") parts of oscillating signals may be obtained using any suitable system or method, such as a Hilbert transform, and may be used for instantaneous phase calculations. Phase may be calculated using an arctangent function of the real and imaginary parts. In some embodiments, a Linear Arctangent Approximation (LAA) algorithm, based on a first-order Lagrange interpolation, can approximate the arctangent function to the fraction of Re and Im in the [−π/4, π/4) range using the following equation:

$$\tan^{-1}\frac{\text{Im}}{\text{Re}} \approx \frac{\pi}{4}\cdot\frac{\text{Im}}{\text{Re}} \tag{1}$$

Figure 7B:
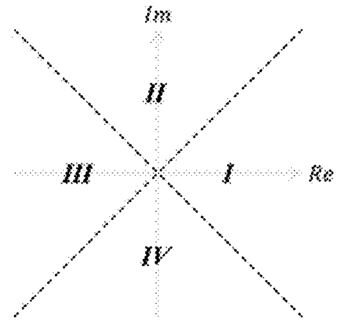
FIG. 7B is a table of mathematical expression of the approximated phases in four quadrants of the imaginary plane.

The range of the LAA may be extended to [−π, π) radians using trigonometric identities, for example as illustrated in FIG. 7B. In some embodiments, the LAA output phase may be normalized by a radian to [−1, 1). In quadrant I, the expression of the normalized approximation algorithm is $$\frac{\text{Im}}{4\text{Re}}$$

which is extended to four quadrants as shown in the table of FIG. 7B. Each of the four quadrants has a unique offset value and fractional form, which may be added to calculate the final phase. The instantaneous phase of complex numbers in the four quadrants in the complex space can be approximated by the offset value plus the fractional form.

Figure 7C:
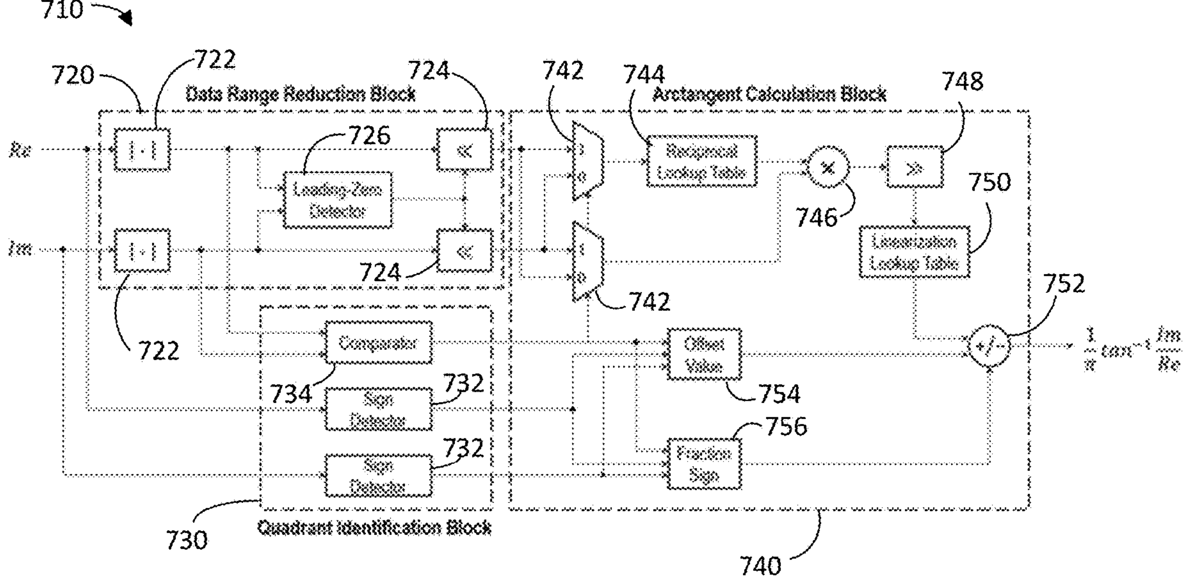
FIG. 7C depicts a schematic of a phase extraction module according to one aspect of the present disclosure.

Turning now to FIG. 7C, an embodiment of a phase extraction module 710 implementing a LAA algorithm, which can achieve efficient yet accurate phase extraction, is illustrated. The phase extraction module 710 may also be referred to as "LAA phase extractor" or "LPE." The phase extraction module 710 may comprise hardware and/or software configured to receive an oscillating signal input and extract the phase. In some embodiments, the phase extraction module 710 may be configured to receive as inputs the real and imaginary components of an oscillating signal and extract the phase using an arctangent function or arctangent approximation. In some embodiments, the phase extraction module 710 may be configured to extract phase using hardware and/or software to perform a LAA. In some embodiments, the phase extraction module 710 may be configured to perform phase extraction in the [0, 0.25) range (normalized) ([0, π/4) radians) in view of the trigonometric identities developed in FIG. 7B.

In some embodiments, the phase extraction module 710 may comprise a data range reduction module 720, quadrant identification module 730, and arctangent calculation module 740. The data range reduction module 720 may comprise any suitable system or method to restrict the largest of the Re and Im inputs to the arctangent calculation module 740 to the range [0.5, 1). In some embodiments, the data range reduction module 720 may comprise circuitry 722 configured to determine the absolute value of the Re and Im inputs. The output of the absolute value circuitry 722 may be coupled with leading-zero detector circuitry 726 and shifters 724. In some embodiments, the absolute values of 10-bit Re and Im inputs range between 0 and 1-2^(−9). For example, if the absolute value of Re=000011111 and the absolute value of Im=000000001, the common four leading zeros are detected, and the two numbers are left-shifted by 4. In this manner, the larger one of the two inputs is restricted between 0.100000000b and 0.111111111b.

The quadrant identification module 730 may comprise any suitable system or method for determining the quadrant of the input to the phase extraction module 710. In some embodiments, the quadrant identification module 730 may comprise sign detectors 732 coupled to the Re and Im inputs, and a comparator 734 coupled to the output of the absolute value circuitry 722. For example, if the Re and Im inputs are both positive and Im is greater than Re, then the input to the phase extraction module 710 belongs in quadrant II (referring to FIG. 7B).

Referring again to FIG. 7C, the outputs from the data range reduction module 720 and the quadrant identification module 730 may be input into the arctangent calculation module 740. The arctangent calculation module 740 may comprise any suitable system or method for calculating phase angle of the input signal using an arctangent approximation. In some embodiments, the arctangent calculation module 740 may comprise input multiplexers (muxes) 742, a reciprocal lookup table ("reciprocal LUT") 744, a multiplication module 746, a shifter 748, a linearization lookup table ("linearization LUT") 750, an offset value module 754, a fraction sign module 756, and an addition module 752.

The input muxes 742 may be coupled with the output of the shifters 724 of the data range reduction module 720 and may be controlled by the output of the comparator 734. The smaller value may be selected by the input muxes 742 for input to the multiplication module 746, which is thus selected as the numerator based on the relationships derived in FIG. 7B. The larger value may be selected by the input muxes 742 for input to the reciprocal LUT 744, based on the relationships derived in FIG. 7B. The reciprocal LUT 744 may comprise any suitable hardware or software memory or storage structure configured to output the reciprocal value of the input. The size of the reciprocal LUT 744 can be reduced in size by restricting the input range using the data range reduction module 720. In one specific non-limiting example, for a 10-bit LAA implementation, the size of the reciprocal LUT 744 can be reduced to $2^8 \times 9$ bits by restricting the input range to [0.5, 1) using the data range reduction module 720.

In some embodiments, the fraction part can be calculated using the multiplication module 746 to multiply the numerator selected by the input muxes 742 with the output of the reciprocal LUT 744, as opposed to a complex division function. The multiplication module 746 may comprise any suitable system or method for multiplying two inputs, for example binary inputs. In some embodiments, the output of the multiplication module 746 may be shifted right by 2 bits by shifter 748, to accomplish dividing the output of the multiplication module 746 by 4 as in Eq. (1). In some other embodiments, the shifter 748 may be coupled between the output of the reciprocal LUT 744 and the multiplication module. In yet other embodiments, the division by 4 may be accomplished with the reciprocal LUT 744.

Figure 7D:
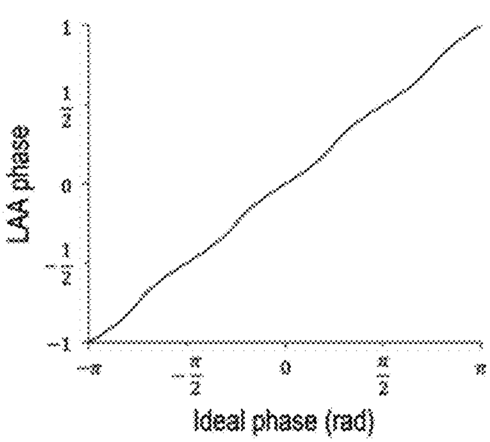
FIG. 7D depicts linear arctangent approximation calculation results according to one aspect of the present disclosure.

The fractions may have nonlinear phase errors due to the nonlinear nature of the arctangent function (see FIG. 7D). In some embodiments, a linearization LUT 750 can be implemented after the reciprocal LUT 744 to compensate for these nonlinear phase errors. The linearization LUT 744 may comprise any suitable hardware or software memory or storage structure configured to output a corrected value corresponding to the input value. In one specific non-limiting example, for a 10-bit LAA implementation, the periodicity of the phase errors can be exploited to reduce the size of the linearization LUT 746 to $2^8 \times 7$ bits. In an exemplary embodiment, the linearization LUT 750 may be coupled with the output of the shifter 748. By placing the linearization LUT 750 after the shifter 748, the bit width of the linearization LUT 750 input, for an exemplary 10-bit LAA implementation, is reduced to 8 bits, reducing the size of the linearization LUT 750.

In some embodiments, an appropriate offset value and fraction sign can be selected (referring to FIG. 7B) by the arctangent calculation module 740. In some embodiments, the arctangent calculation module 740 may comprise an offset value module 754 for providing the offset value corresponding to the input to the phase extraction module 710, for example as shown in FIG. 7B. The offset value module 754 may comprise any suitable hardware or software for determining, using the output of the comparator 734 and sign detector(s) 732, the offset value and outputting the offset value or an indication of the offset value. In some embodiments, the offset value module 754 may comprise a hardware or software lookup table, a memory (ROM, RAM, etc.), or the like. In some embodiments, the offset value module 754 may comprise logic which outputs an indication to the addition module 752 regarding what value to use as an offset.

In some embodiments, the arctangent calculation module 740 may comprise a fraction sign module 756 for providing a signal indicating whether the fraction determined in the arctangent calculation module 740 should be added to or subtracted from the determined offset value 754, for example as shown in FIG. 7B. The fraction sign module 756 may comprise any suitable hardware or software for determining or otherwise outputting an indication of the fraction sign. In some embodiments, the addition module 752 may use the indication of the faction sign as a control input to control the addition and/or subtraction operations.

Figure 7E:
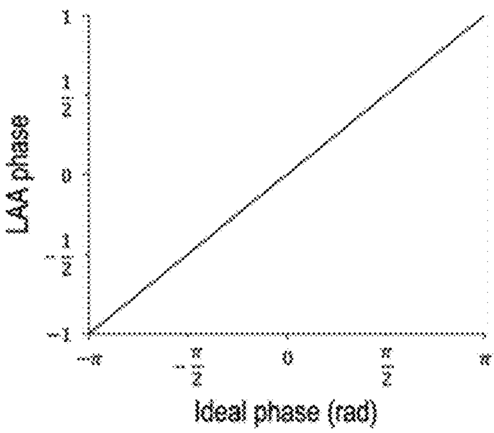
FIG. 7E depicts the corrected and linearized linear arctangent approximation calculation results of FIG. 7D.
Figure 7F:
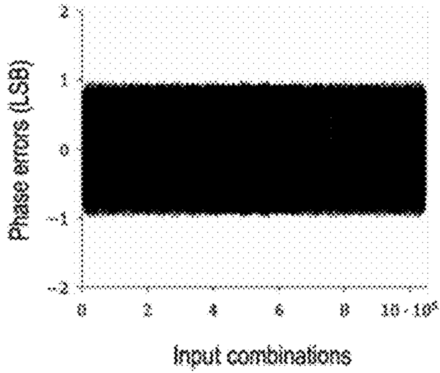
FIG. 7F depicts phase errors of linear arctangent approximation calculations.

With the nonlinear phase errors (discussed above) corrected via the linearization LUT 750, the linearized fraction can then be added to, or subtracted from the determined offset value (depending on the fraction sign module 756 output) using the addition module 752, to reconstruct the range. In some embodiments, the output range of the phase extraction module may be normalized to [−1, 1). The final phase value can then be generated as shown in FIG. 7E. As a result, the phase extraction module 710 calculates the arctangent function with phase errors less than one least significant bit ("LSB"). FIG. 7F shows the LAA phase errors for $2^{20}$ possible combinations of 10-bit Re and Im inputs, with respect to the baseline floating-point phases, which can be calculated using an ideal arctangent function.

Figure 7G:
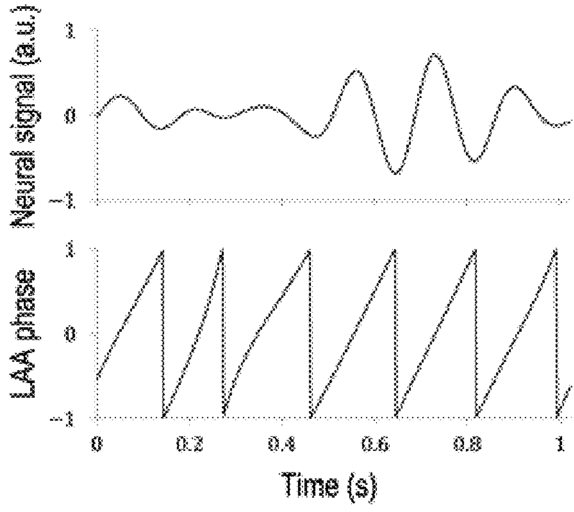
FIG. 7G depicts phase extraction utilizing a linear arctangent approximation algorithm according to one aspect of the present disclosure.

For comparison, an FPGA-based design for phase extraction previously used two redundant adders for quadrant identification, while tabulating the non-linear phase error, which can include an additional multi-bit adder for final phase calculation. Compared to the FPGA-based design, the systems and methods described herein employ algorithms and phase error cancellation method that allow a reduction in the number of required arithmetic units, while at the same time achieving last-bit accuracy, reduced size, and low power. The systems and methods described herein have been successfully verified on neurophysiological signals. Referring to FIG. 7G, an example is shown of LAA phase extraction from theta-band oscillations (4-8 Hz) in an intracranial EEG (iEEG) signal recorded from a patient with epilepsy.

Figure 7H:
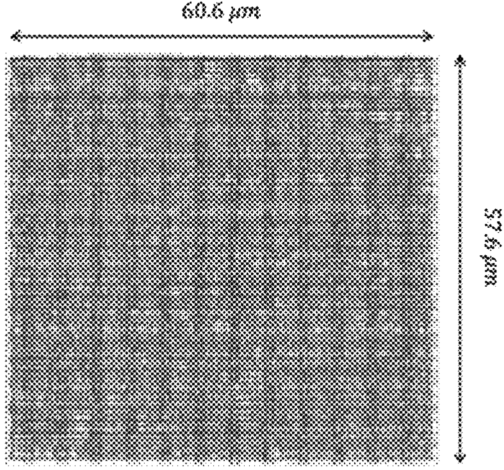
FIG. 7H depicts a chip layout of an integrated circuit according to one aspect of the present disclosure.

In one specific non-limiting example, the proposed LAA architecture was implemented in Verilog HDL, synthesized with Synopsys Design Compiler, and placed and routed using Cadence Innovus in a 65-nm low-power CMOS process. A 10-bit LAA hardware was implemented. The 64-channel input neural signals sampled at 1 kS/s per channel were fed to the LAA module according to the embodiments described herein. The LAA hardware (FIG. 7H) consumed only 162 nW of power at 0.8V supply for 64-channel phase extraction, in a small silicon area of 3,491 $\mu m^2$. This LAA implementation is more energy- and area-efficient than conventional FPGA or CORDIC designs and can operate at high speeds (e.g., up to 52.6 MHz in some embodiments) with no latency overhead.

Hardware Design for Phase Based Synchrony Metrics

Effective brain stimulation may target and change network synchrony. Depending on the specific disease and circuit, "synchrony" might mean coherence, or phase-based features such as phase-amplitude coupling ("PAC"), phase locking value ("PLV"), amplitude-based features such as amplitude correlations, or a related metric. The model described herein provides systems and methods, such as integrated circuits, for LAA-based phase and amplitude feature extraction (PAC and PLV) following signal conditioning. The proposed designs can efficiently compute the phase metrics of PAC and PLV for use with controlling neural oscillation synchrony between any selected subset of neural channels (e.g., two channels for cross-regional PLV or PAC calculation, one channel for single-region cross-frequency PAC calculation). The designs can be scaled to high-channel-count architectures (e.g., 64 channels or more). Implementations, including circuit implementations, of the PAC and PLV features using the provided LAA architecture and several techniques to improve the energy efficiency are described below. For simplicity of illustration, only two amplifiers are shown in the signal conditioning modules, while the proposed feature extraction circuits can easily extract phase features from a higher number of input channels, e.g., using time-division multiplexing ("TDM").

There are various methods to measure phase-amplitude coupling (e.g., modulation index, mean vector length, heights ratio). In some embodiments, the mean vector length ("MVL") approach may be utilized, in view of its good trade-off between performance and hardware complexity.

$$z(t) = A_{f_A} e^{i\theta_{f_P}} \tag{2}$$

$$PAC = |\overline{z(t)}| = \frac{1}{N}\sqrt{\left(\sum_{i=1}^{N} A_{f_{A,i}} \sin\theta_{f_{P,i}}\right)^2 + \left(\sum_{i=1}^{N} A_{f_{A,i}} \cos\theta_{f_{P,i}}\right)^2}$$

The length of a complex vector z(t) represents the instantaneous amplitude of the signal in the amplitude-modulated frequency band (denoted by $f_A$), while the instantaneous phase in the phase-modulating frequency band (denoted by $f_P$) is represented by the vector angle. Strong PAC can cause an asymmetric distribution of vectors (higher amplitude of $A_{f_A}$ at certain $\theta_{f_P}$ phases), resulting in a non-zero average vector length. PAC and PLV features may be extracted on a window-by-window basis, and N is the number of samples considered in each window. In an exemplary embodiment, if the data rate is 1 kS/s (1000 Samples/second) and the window size is one second, N is 1000 samples.

Figures 8A, 8B:
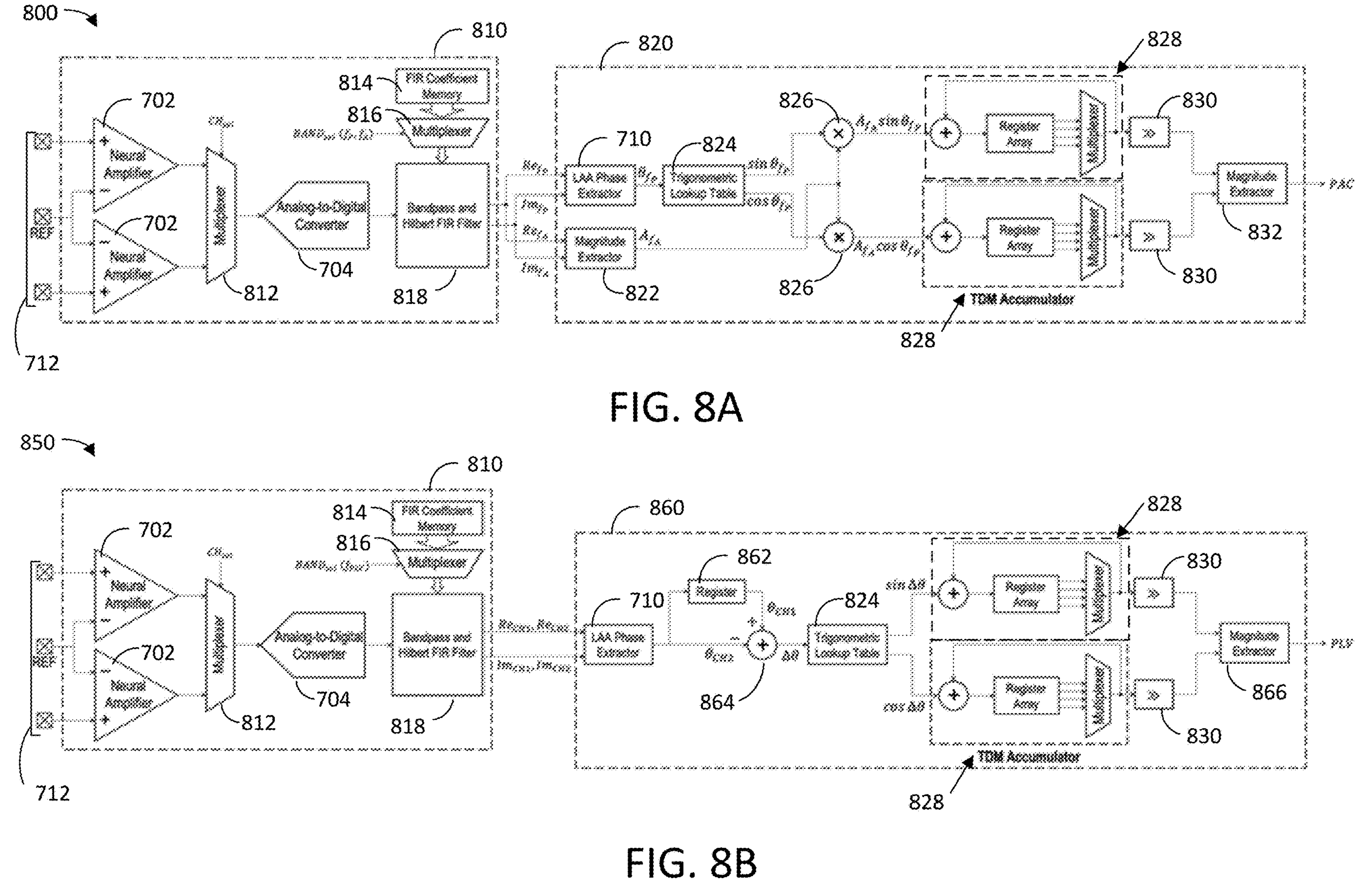
FIG. 8A depicts a first schematic of a signal conditioning module and a determination module according to one aspect of the present disclosure.
FIG. 8B depicts a second schematic of a signal conditioning module and a determination module according to one aspect of the present disclosure.

Referring to FIG. 8A, an exemplary embodiment of PAC extraction system 800 is shown. The PAC extraction system 800 may comprise a signal conditioning module 810 and a PAC determination module 820. The signal conditioning module 810 may comprise systems and/or methods configured to digitize, filter, and determine real (Re) and imaginary (Im) components of one or more oscillating input signals. In some embodiments, the input signal (e.g., a neural signal (bipolar or monopolar)) in one or more channels may be initially amplified by an amplifier 702, for example a low noise amplifier ("LNA"). An optional multiplexer ("mux") 812 may allow selection of input channel. The amplified signal may then be digitized using an ADC 704, and bandpass filtered in two different frequency bands ($f_A$, $f_P$). The real ($Re_{f_P}$, $Re_{f_A}$) and imaginary ($Im_{f_P}$, $Im_{f_A}$) parts of the bandpass filtered signals are then extracted using Hilbert filters. In the illustrated non-limiting example, a single digital finite impulse response ("FIR") filter with a TDM scheme may be implemented by the filter module 818 to perform both bandpass filtering and Hilbert transform for multi-channel inputs (i.e., PAC features can be extracted from multiple individual channels or multiple pairs of input channels using a single multiplexed hardware). FIR filter coefficients can be retrieved from a memory 814, such as an on-chip memory, and provided to the filter module 818 through a band selecting multiplexer 816.

The PAC determination module 820 may comprise systems and/or methods configured to determine PAC using the real ($Re_{f_P}$, $Re_{f_A}$) and imaginary ($Im_{f_P}$, $Im_{f_A}$) parts of the filtered signals provided by the signal conditioning module 810. In some embodiments, the PAC determination module 820 may comprise a phase extraction module 710 and a magnitude extraction module 822, which may be used to calculate the instantaneous phase $\theta_{f_P}$ and magnitude (also referred to as amplitude) envelope $A_{f_A}$, respectively. The magnitude extraction module 822 may comprise any suitable system or method for calculating or approximating the magnitude of the input value(s). For example, the magnitude extraction module 822 may be configured to perform $\ell^{\infty}$-norm approximation or $\ell^{2}$-norm calculation.

The sine and cosine of the phase can be read from a trigonometric LUT 824, which may comprise any suitable hardware or software memory or storage structure configured to output trigonometric values based on its input value. The periodicity of the trigonometric functions can be exploited to reduce the trigonometric LUT 824 input range to [0, π/2). The sine and cosine values may then be multiplied, using a suitable multiplication system or method 826, by the magnitude envelope from the magnitude extraction module 822 and accumulated over a predefined window (N samples) according to Eq. (2). Any suitable system or method may be used to accumulate the values. In some embodiments, a TDM accumulator 828 may be used to accumulate the values and may comprise an addition module coupled with a register array and multiplexer, with the output of the multiplexer used as an input to the addition module. In the illustrated non-limiting example, two TDM accumulators 828 were used in the sine and cosine signal paths. This TDM approach can allow a single feature extraction module to perform multiple feature extractions. Thus, significant hardware savings can be achieved since only the number of registers and multiplexer inputs scale up with the number of features.

The output of the TDM accumulator(s) 828 may be right-shifted 830, and the final PAC value may be extracted by magnitude extraction module 832. The right shift performs division by N in Eq. (2), and the amount of shifting depends on the window size N. N may be set to a power of 2 so that a complex divider circuit can be replaced by bit shifting. For example, if N=1024 (=$2^{10}$), the output of accumulators is right shifted by 10. PAC extraction according to Eq. (2) requires two amplitude (e.g, Euclidean norm) calculations. In some embodiments, the magnitude extraction modules 822, 832 may be configured to approximate the amplitude using $\ell^{\infty}$-norm: magnitude extraction module 822 approximates $A_f$, and magnitude extraction module 832 approximates the root of squaring of the summations in Eq. (2).

Referring to FIG. 8B, an exemplary PLV extraction system 850 is shown. The PLV extraction module 850 may be configured to use a mean phase coherence algorithm:

$$PLV = \frac{1}{N}\sqrt{\left(\sum_{i=1}^{N}\sin\Delta\theta_i\right)^2 + \left(\sum_{i=1}^{N}\cos\Delta\theta_i\right)^2} \quad (3)$$

In the PLV extraction system 850 shown in FIG. 8B, neural signals from two different channels (e.g., two regions of the brain) are amplified, digitized, and bandpass filtered over a selected band ($f_{PLV}$) using the signal conditioning module 810. Then, Hilbert filter outputs are fed to the PLV determination module 860. The phase extraction module 710 estimates the instantaneous phase values $\theta_{CH1}$ and $\theta_{CH2}$. The cross-channel phase difference Δθ may be determined using suitable systems or methods, for example the illustrated register 862 and addition module 864. Next, the sine and cosine of cross-channel phase difference Δθ are determined by a trigonometric LUT 824 and accumulated over time using the TDM accumulators 828. The shifters 830 and magnitude extraction module 866 are configured to calculate the PLV feature based on Eq. (3). Shifters 830 may perform a right shifting for division by N as described for the PAC determination module 820, and magnitude extraction module 866 approximates the root of squaring of the summations in Eq. (3).

Figure 8C:
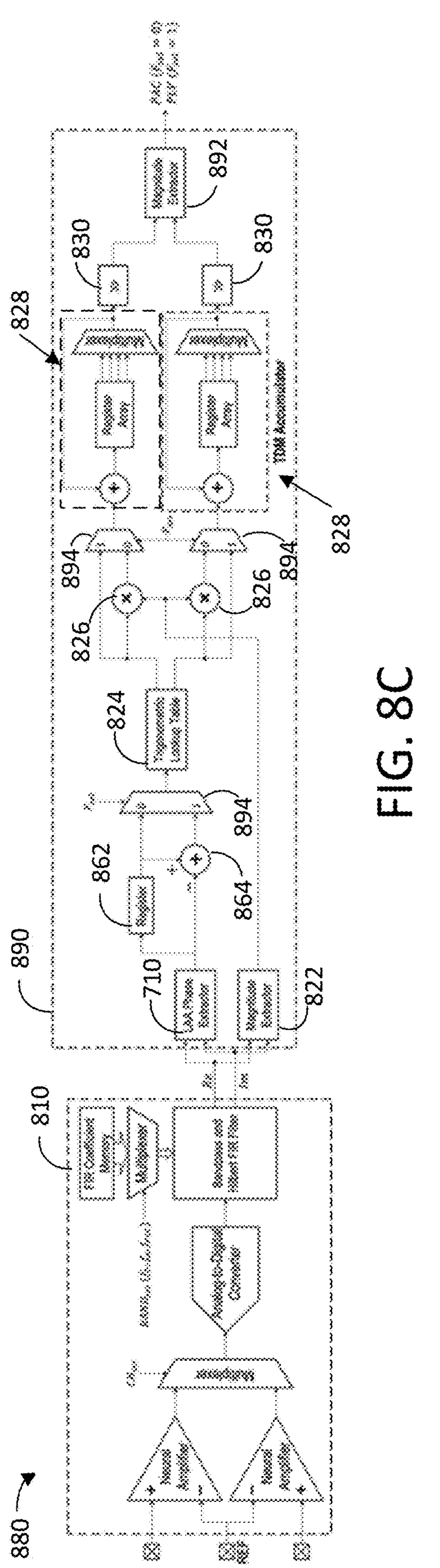
FIG. 8C depicts a third schematic of a signal conditioning module and a determination module according to one aspect of the present disclosure.

In some embodiments, common hardware blocks can be shared between the PAC determination module 820 and PLV determination module 860 to further reduce the power consumption and chip area. Referring to FIG. 8C, an exemplary multi-feature extraction system 880 is shown. The multi-feature extraction system 880 may comprise a unified feature determination module 890, which may comprise shared components of the PLV determination module 860 and PAC determination module 820. Multiplexers 894 may be used and configured to select the appropriate data to output based on the desired function, e.g., PAC or PLV determination (e.g. selection input Fsel=0 for PAC, Fsel=1 for PLV). The magnitude extractor 892 may be configured to extract the final PAC or PLV value according to Eq (2) or Eq (3) as described above, using suitable systems or methods.

A similar generalization can apply to amplitude-amplitude correlation or coupling ("AAC"), calculated within or across frequency bands.

$$AAC = \frac{N\sum_{i=1}^{N}A_{x,i}A_{y,i} - \sum_{i=1}^{N}A_{x,i}\sum_{i=1}^{N}A_{y,i}}{\sqrt{N\sum_{i=1}^{N}A_{x,i}^2 - \left(\sum_{i=1}^{N}A_{x,i}\right)^2}\sqrt{N\sum_{i=1}^{N}A_{y,i}^2 - \left(\sum_{i=1}^{N}A_{y,i}\right)^2}} \quad (4)$$

In the above equation, $A_x$ and $A_y$ denote the instantaneous amplitude/magnitude for two selected channel-band combinations denoted x and y.

The outputs of any of these feature extraction systems (PLV, PAC, etc.) can be routed to stimulation control for, e.g., phase-locked stimulation at a chosen band and angle to suppress a neurological symptom. The extracted features may be compared to predefined thresholds, may be fed to a machine-learning processor (classifier) to determine the pathological brain state of the patients to trigger electrical stimulation, and the like.

As illustrated in the equations above, these connectivity metrics can be defined by Euclidean distance (i.e., $\ell^{2}$-norm calculations). Moreover, PAC and AAC extraction can include magnitude envelope calculations. These calculations can be complex to implement in hardware due to the use of root sum squared calculations. In some embodiments, the magnitudes for PAC and PLV may be estimated, for example by using a hardware-efficient $\ell^{\infty}$-norm approximation. This further reduces the computational cost and power consumption of various embodiments of the present technology, while precisely tracking PAC and PLV over time. In some embodiments, this may be generalized to the AAC case by modification to the routing of signals.

Figures 9, 10:
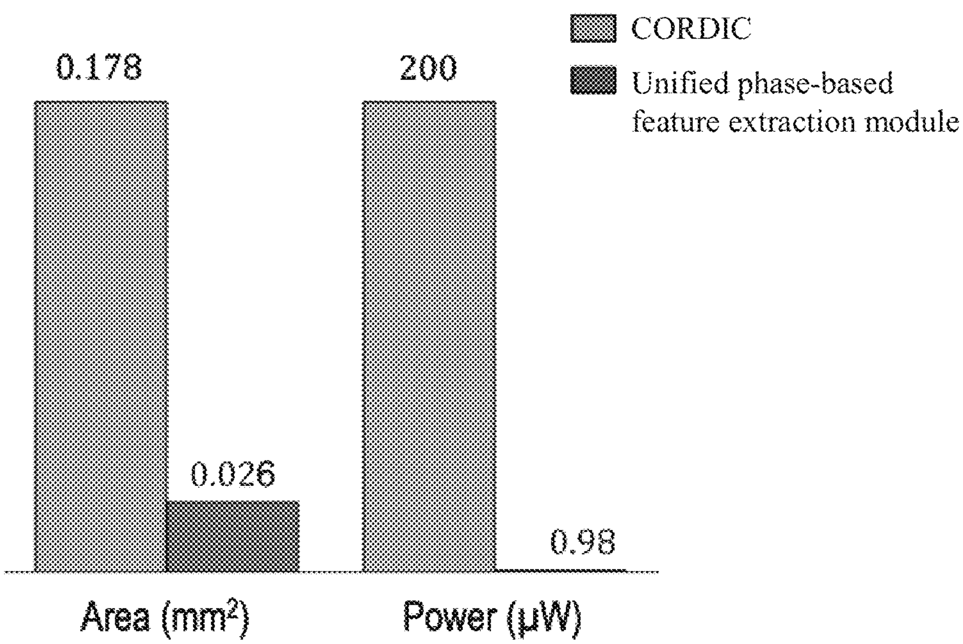
FIG. 9 depicts a table of exemplary performance results of a synchrony metric calculation system according to one aspect of the present disclosure.
FIG. 10 depicts a graph of exemplary performance results of the synchrony metric calculation system.

By way of example, using a 10-bit model of the proposed unified feature determination module 890 shown in FIG. 8C, both PAC and PLV features for a seizure classification task were extracted, in order to verify the impact of the LAA phase and $\ell^{\infty}$-norm approximations. As a baseline for comparison, accurate values of features can be used by employing floating-point arctangent function and $\ell^{2}$-norm operator (Eq. (2) and (3)). While a combination of different feature types (e.g., spectral power, line length) can boost the classification performance, only phase-based features were tested in this task to better examine the impact of the approximations. FIG. 9 summarizes the results and shows that the provided feature approximations cause no significant performance loss.

This example correlation analysis shows that the provided feature approximations with 10-bit accuracy are statistically identical to the actual features with infinite accuracy. The PAC correlation is relatively lower due to the small amplitudes of high-gamma oscillations and the limited dynamic range of the ADC used in this simulation, but it is sufficient to achieve a reasonable classification accuracy.

Figure 8D:
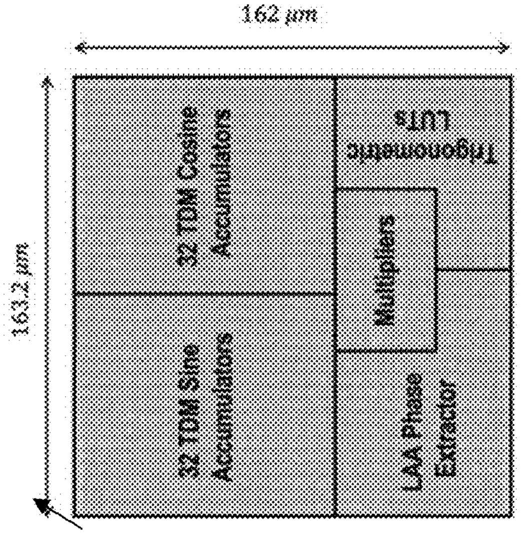
FIG. 8D depicts a chip layout of an integrated circuit according to one aspect of the present disclosure.

Referring now to FIG. 8D, the unified feature determination module 890 of FIG. 8C was implemented in a 65-nm low-power process. The module was designed to perform 32 feature extractions (PAC, PLV, or combinations of the two). The number of extractions can be scaled up at the cost of a small increase in multiplexing hardware and registers in TDM accumulator 828. FIG. 10 compares the provided LAA-based feature extraction hardware against a conventional CORDIC-based design in terms of area and power consumption.

The unified feature determination module 890 achieves a notable decrease in area and achieves a ~200× improvement in power consumption. The provided hardware-friendly phase and magnitude approximators allow the unified feature determination module 890 (and alternatively the PAC determination module 820 or PLV determination module 860) to be clocked at a relatively low frequency (e.g., approximately 64 kHz) for 32 feature extractions (1 kS/s per channel), thus enabling a significant saving in the dynamic power consumption without compromising the feature extraction accuracy.

ASIC Design for Synchrony Metrics and Stimulation

The systems and method described herein may be used to determine phase-based metrics of one or more oscillating signals, and to provide an electrical stimulation in accordance with the determined metrics. Referring to FIG. 11, an application specific integrated circuit ("ASIC") 1100 for measuring one or more input signals and outputting one or more control signals in accordance with the measured input(s) is illustrated. The ASIC 1100 may be configured to provide communication with an external device, for example via wired or wireless interface, such as Bluetooth, NFC, Ethernet, and the like. In some embodiments, the ASIC 1100 may comprise a signal conditioning module 810 (e.g., signal detection module 114 of FIG. 1), a Phase Synchrony Processor 1130 (e.g., processor 108 of FIG. 1), and a stimulator module 1140 (e.g., a signal generation module 114 of FIG. 1). The ASIC 1100 may take as inputs 1104 one or more oscillating signals (e.g., bipolar or monopolar), for example from one or more DBS leads 1102. The ASIC 1100 may provide one or more electrical signals as outputs 1106 (e.g., bipolar or monopolar), for example to one or more DBS leads 1102.

The input signal(s) may be conditioned by the signal conditioning module 810. The components of the signal conditioning module 810 may be selected to provide good gain matching among channels to allow for cross-regional biomarker extraction. The input signal(s) may be amplified by the amplifier 702. In some embodiments, the amplifier 702 may comprise a closed-loop chopper-stabilized LNA ("chopper LNA"), comprising up- and down-modulation 1108. In some embodiments, the amplifier 702 may comprise an amplifier for each input. For example the ASIC 1100 may comprise a 16-channel input, and the amplifier 702 may comprise 16 closed-loop chopper-stabilized LNAs.

The output(s) of the chopper LNA 702 may be multiplexed 812 to an integrator 1110. The mux 812 may, for example, comprise a 16:1 multiplexer. The mux 812 and chopper LNAs 702 may be configured to allow addressing of the LNAs in any user-defined order to allow flexible channel combinations for synchrony extractions. In some embodiments, the integrator 1110 may comprise a Gm-C integrator. The integrator 1110 may provide additional amplification to the output of the chopper LNA 702. The integrator 1110 may be configured to perform lowpass filtering to prevent signal aliasing during sampling in the ADC 704. After amplification and possible integration, the signals are then digitized to any suitable bit width by the ADC 704. In some embodiments, the ADC 704 may comprise a 10-bit SAR ADC.

The output of the ADC 704 may then be filtered and transformed by the filter module 818 to provide suitable input to the Phase Synchrony Processor 1130 and/or unified feature determination module 890. In some implementations, the processor 108 (see FIG. 1) may comprise the Phase Synchrony Processor 1130 and the filter module 818. Filtering may comprise, for example, decimation (×4 in some embodiments) and bandpass filtering. Transformation may comprise, for example a Hilbert Transform. In some embodiments the signal conditioning module 810 may comprise a programmable threefold FIR filter configured to decimate, bandpass filter, and Hilbert transform the converted input signals 1104 (i.e., from ADC 704). In some embodiments, the threefold FIR filter may further comprise shared hardware, which may help realize chip area reduction.

The output of the signal conditioning module 810 may be sent to a Phase Synchrony Processor ("PSP") 1130. The PSP 1130 may comprise suitable hardware and/or software configured to extract (e.g., simultaneously) various neural biomarkers, for example instantaneous phase, amplitude envelope, PLV, PAC, spectral energy ("SE"), and/or the like. In some embodiments, the PSP 1130 may comprise a unified feature determination module 890 configured to perform the various neural biomarker extractions. The PSP 1130 may further comprise a phase-locking detector 1116, which may comprise suitable hardware and/or software configured to select (e.g., via multiplexer(s)) and compare biomarkers to predefined thresholds 1114 and/or randomly generated thresholds 1112.

In some embodiments, the PSP 1130 may further comprise a stimulation control 1120 coupled with the output of the phase-locking detector 1116. The stimulation control 1120 may comprise suitable hardware and/or software configured to provide appropriate control signals to the stimulator module 1140. The stimulator module 1140 may comprise suitable hardware and/or software configured to output an appropriate electric signal on the one or more outputs 1106, for example to stimulate one or more regions of a brain, based on one or more control inputs from the stimulation control 1120.

Figure 12A:
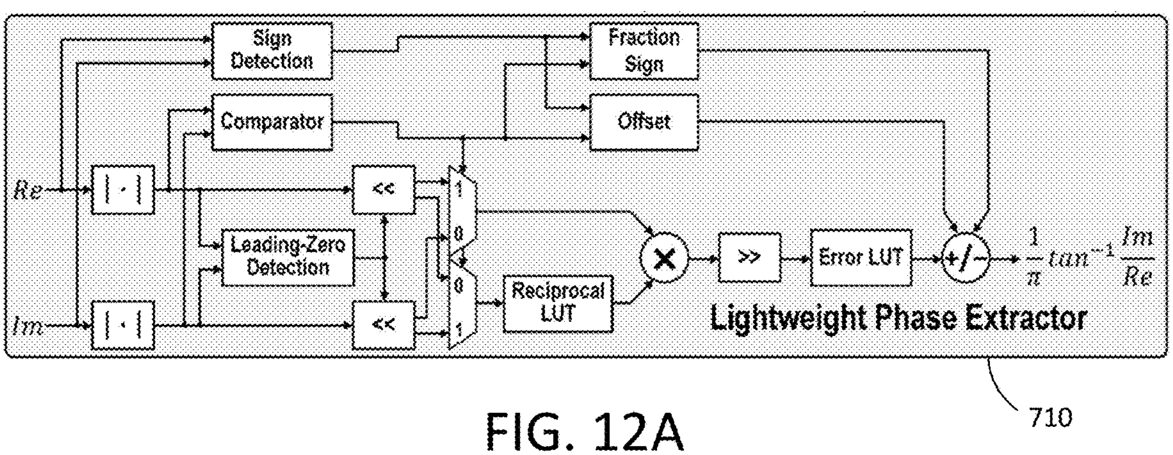
FIG. 12A depicts a schematic of a phase extraction module according to one aspect of the present disclosure.
Figure 12B:
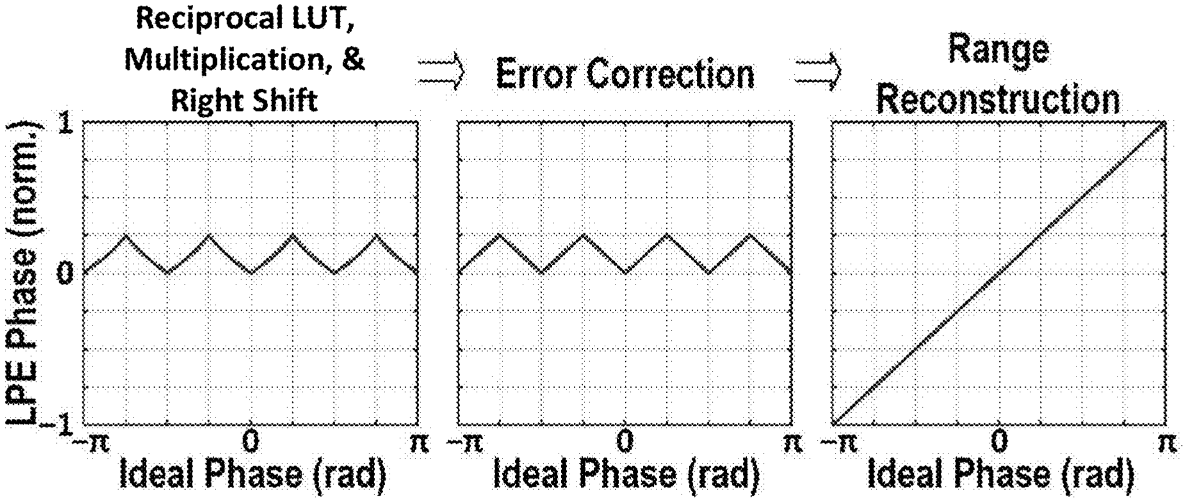
FIG. 12B depicts phase errors, error correction, and phase with linear approximation according to one aspect of the present disclosure.
Figure 12C:
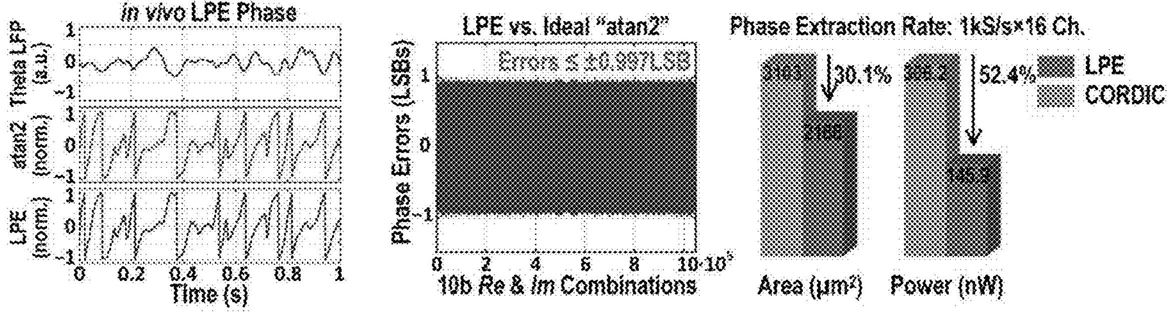
FIG. 12C depicts experimental measurement comparisons, phase errors, and area and power comparisons according to one aspect of the present disclosure.

Referring to FIG. 12A, an implementation of the ASIC 1100 phase extraction module 710 is illustrated. As previously described, such implementations reduce hardware complexity and overcome the power-accuracy-latency drawbacks of conventional methods. FIG. 12B shows the resulting periodic phase errors of the right-shifted output of the multiplication module, error correction after the linearization LUT (also referred to as "Error LUT"), and range reconstruction. In this implementation, the phase extraction module 710 is configured to provide 10-bit phase outputs normalized to $[-1, 1)$. FIG. 12C shows sub-LSB phase errors at the output of the phase extraction module 710, with respect to the ideal arctangent function. FIG. 12C further shows the oscillatory phase of theta-band LFP measured in-vivo from a Long-Evans rat. For comparison, a last-bit accurate 10-bit unrolled CORDIC was implemented with bit-width optimization and input range reduction, similar to the technology described herein. FIG. 12C shows that the phase extraction module 710 described herein achieves a greater than 30% and 50% improvements in area and power as compared to the CORDIC, respectively.

Figures 13A, 13B:
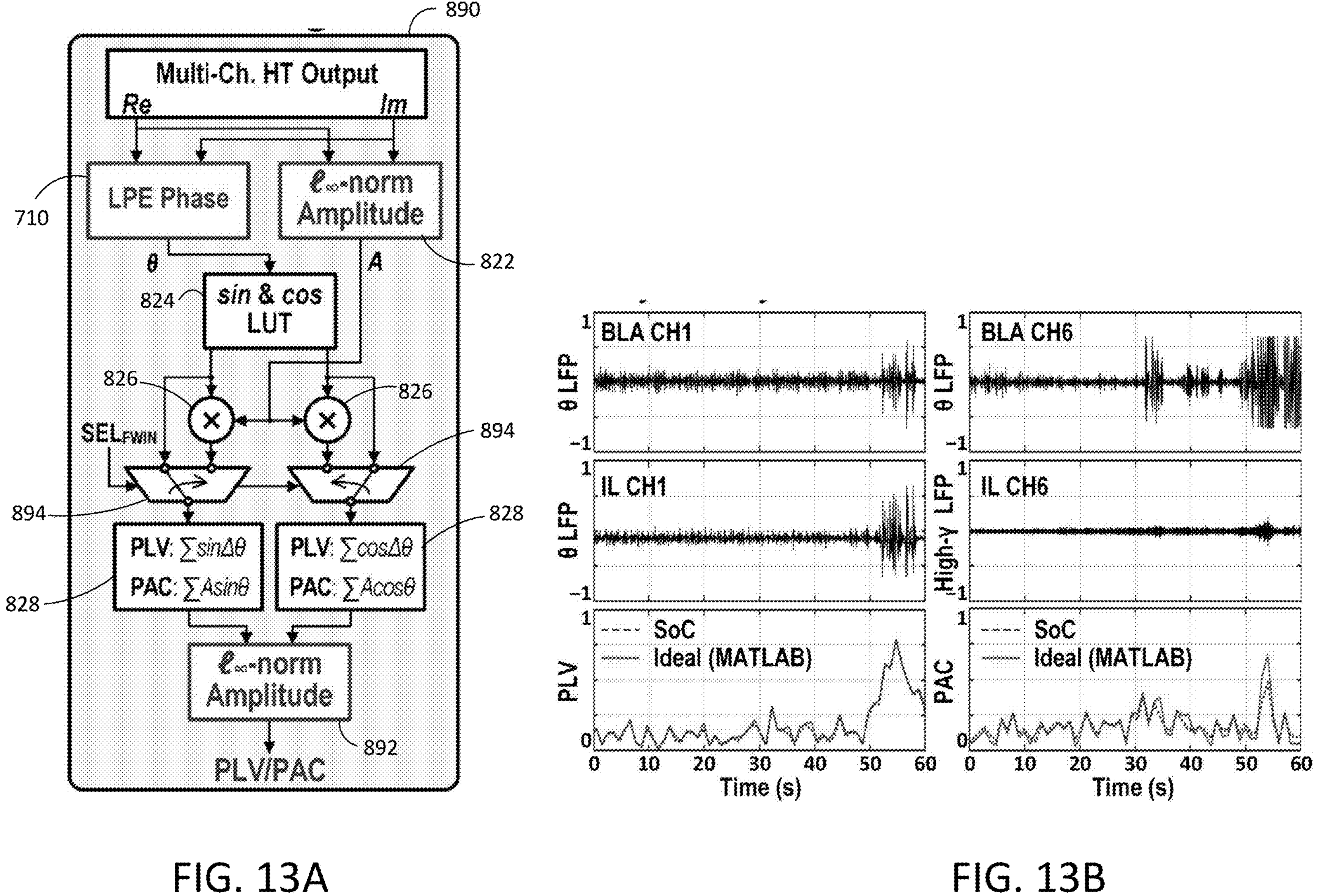
FIG. 13A depicts a schematic of a determination module according to one aspect of the present disclosure.
FIG. 13B depicts graphs of exemplary performance results of the determination module of FIG. 13A.

Referring to FIG. 13A, an implementation of the ASIC 1100 unified feature determination module 890 is illustrated, according to previously described embodiments. As previously described, the $\ell$-norm approximation may be implemented for the amplitude envelope in PAC and PLV, to improve hardware efficiency and avoid use of complex Euclidean norms. FIG. 13B shows results of experimental measurements of cross-regional PLV and PAC taken with an embodiment of the ASIC 1100, which closely track the ideal features (e.g., as provided by mathematical software). The PLV and PAC measurements were based on signals from the infralimbic cortex (IL) and basolateral amygdala (BLA). Referring to FIG. 13B, the top four charts show bandpass filtered neural oscillations in the theta and high gramma frequency bands. The PLV chart on the bottom left shows the degree of phase locking between BLA CH1 and IL CH1 in the theta band. The PAC chart on the bottom right shows the degree of coupling between the theta phase of BLA CH6 and high-gamma amplitude of IL CH6.

Figure 13C:
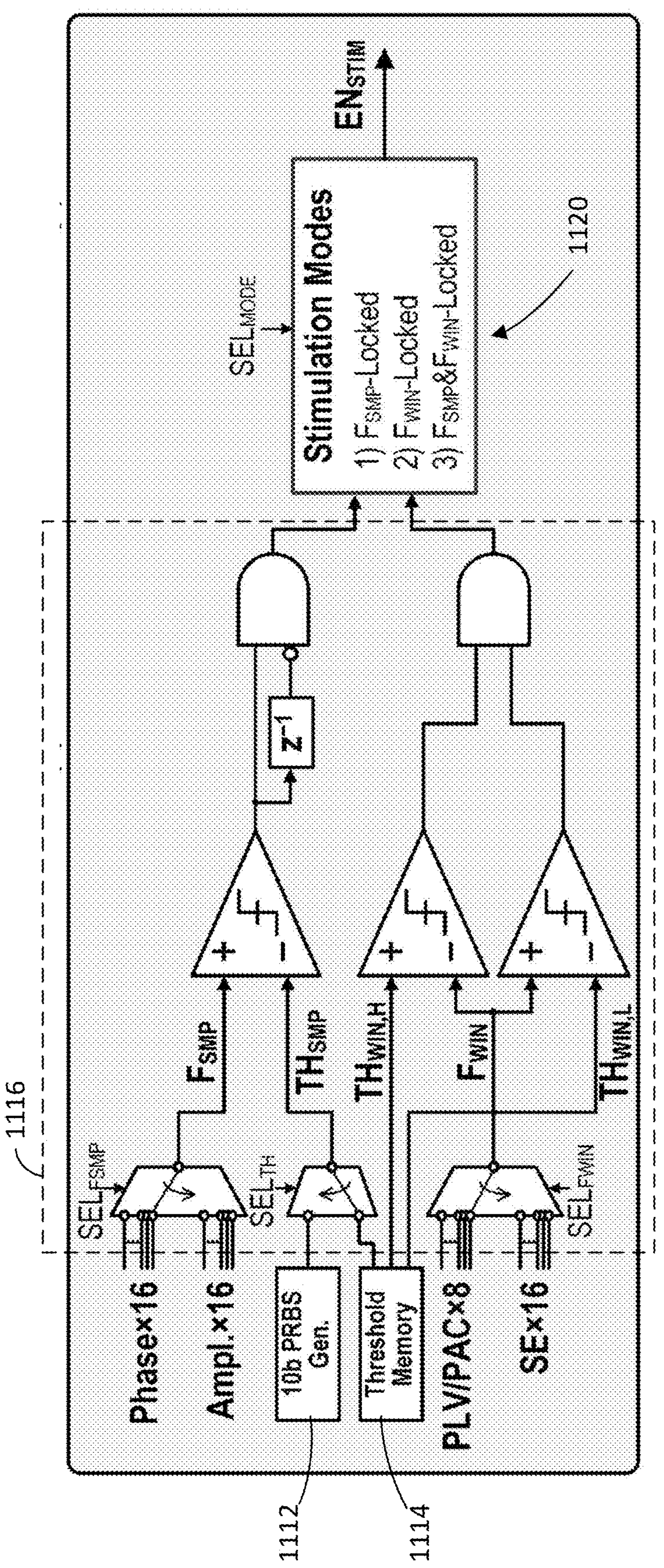
FIG. 13C depicts a schematic of a phase-locking detector and stimulation control according to one aspect of the present disclosure.

Referring to FIG. 13C, additional features of the ASIC 1100 phase-locking detector 1116 and stimulation control 1120, which provide flexible stimulation control, are illustrated. In some embodiments, the phase-locking detector may be configured to support various stimulation modes by thresholding the per-sample feature ($F_{SMP}$, e.g., phase/amplitude at 1 kHz), windowed feature ($F_{WIN}$, e.g. PLV, PAC, and/or SE at 1-4 Hz), or a combination of the two. The various multiplexers may be control by a window select ($SEL_{FWIN}$), per-sample feature select ($SEL_{FSMP}$), and threshold select ($SEL_{TH}$). In some embodiments, a random threshold generator 1112 may provide random thresholds, which in some embodiments may be use for synchrony disruption to provide various therapeutic effects. In some embodiments, the random threshold generator 1112 may comprise a 10-bit pseudo-random binary sequence threshold generator. In some embodiments, the threshold memory 1114 may comprise any suitable hardware and/or software configured to store predefined thresholds. The stimulation control 1120 may comprise any suitable hardware and/or software configured to provide control signal(s) to the stimulator module 1140.

According to an exemplary embodiment, the implementation of the PSP 1130 in the ASIC 1100 consumes 9.69 μW (including FIR) at a 0.85V supply for determining 8 PLV/PAC features, achieving a greater than 60.7% savings per feature compared to existing designs.

Figure 14:
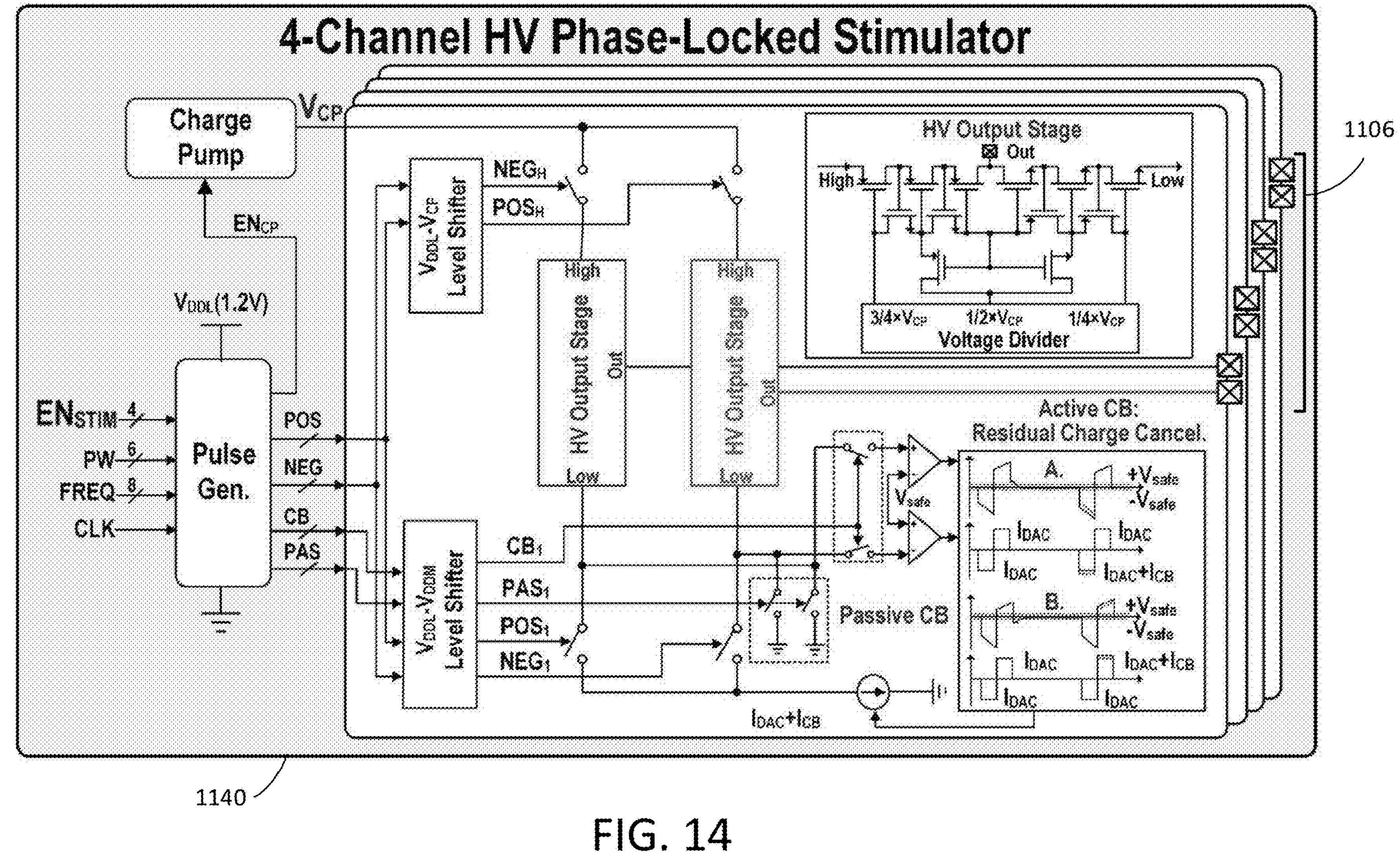
FIG. 14 depicts a schematic of a stimulator module according to one aspect of the present disclosure.

Referring to FIG. 14, an implementation of the stimulator module 1140 is illustrated. The stimulator module 1140 may comprise a programmable neurostimulator (e.g., 30-440 μA), for example a 4-channel programmable neurostimulator. The stimulator module 1140 may comprise an output driver comprising a stacked H-bridge architecture with active and passive charge balancing ("CB"), and may provide stimulation via the outputs 1106.

Referring to FIGS. 15A-C, measurement results of the ASIC 1100 analog front end ("AFE"), comprising amplifier 702 through ADC 704, and stimulator module 1140 are shown. Referring to FIG. 15A, a low input-referred noise ("IRN") of 0.88 μVrms (including the ADC 704) was achieved in the 1-500 Hz band, consuming 2.78 μW/channel. Referring to FIG. 15B, the 16-channel gain matching (<0.1% mid-band) and gain programmability (53-61 dB) were further demonstrated. Referring to FIG. 15C, for an intentional 50% mismatch in stimulation pulse width, the CB reduces the residual voltage to less than ±4 mV through compensation currents and passive discharging.

Referring back to FIGS. 6A-6D, stimulation was targeted at a specific phase (180°) of theta-band LFP (4-8 Hz) that is known to correlate with fear- and anxiety-like behavior. Theta-band phase- and PLV-locked stimulation is further demonstrated. FIG. 6D shows 16-channel LFP recording and phase-locked stimulation in two modes (phase-locked stimulation, and phase-locked & PLV-locked stimulation. For example, a predefined per-sample feature threshold ($TH_{SMP}$) was set to 180°, and predefined windowed feature thresholds were set at 0.5 ($TH_{WIN,L}$) and 1 ($TH_{WIN,H}$) (e.g., the predefined therapeutic range in this example being between 0 and 0.5). In the second experiment, stimulation was triggered when both phase locking and PLV locking were detected. For both experiments, the maximum stimulation frequency was set to 6 Hz, and the phase-locking detector was controlled such that phase wrapping did not trigger the stimulation.

FIG. 16 shows ASIC 1100 area and power breakdowns and comparison to other state-of-the-art solutions. The exemplary 16-channel ASIC 1100 occupies an area of 2.24 $mm^2$ and consumes 60 μW. Systems and methods according to embodiments of the present technology allow for integration of phase-locked stimulation while providing various stimulation modes in response to cross-regional phase- and amplitude-based neural biomarkers, which is an improvement over and not found in prior solutions. Systems and methods according to various embodiments of the present technology may be used for, among other things, treating a range of network-based disorders, including depression, anxiety, OCD, and movement disorders.

As appreciated from description above, herein provided systems and methods utilize a novel approach and have a broad range of applications, including for treatment of patients with various neurological and psychiatric disorders. Features suitable for such combinations and sub-combinations would be readily apparent to persons skilled in the art upon review of the present application as a whole. The subject matter described herein and in the recited claims intends to cover and embrace all suitable changes in technology.

We claim:

1. A method for controlling connectivity between two or more brain regions of a subject, the method comprising:

receiving signals corresponding to a connectivity between a first target region and a second target region in a subject's brain;

determining, from the received signals, a connectivity level between the first target region and the second target region; and delivering at least one stimulation pulse to at least one of the first and second target regions if the connectivity level is outside of a predetermined range.

2. The method of claim 1, wherein if the connectivity level is within the predetermined range, no stimulation is delivered.

3. The method of claim 1, wherein the received signals are local field potentials within at least one predetermined frequency band.

4. The method of claim 3, wherein the at least one predetermined frequency band is in a range of one of 5-15 Hz, 15-30 Hz, or 30-200 Hz.

5. The method of claim 3, wherein the connectivity level is a phase locking value determined from the phase of the received signals from the first target region and the second target region.

6. The method of claim 3, wherein the connectivity level is a phase-amplitude coupling value determined from the phase of the received signals from the first target region and the amplitude or power of the received signals from the second target region.

7. The method of claim 1, wherein the at least one stimulation pulse is time-locked to a phase of an oscillation from the first target region or the second target region.

8. The method of claim 7, wherein the at least one stimulation pulse is delivered when the phase of the oscillation is at 180 degrees.

9. The method of claim 7, wherein the at least one stimulation pulse is delivered at a phase that is randomized from the phase of a previously delivered pulse.

10. The method of claim 1, wherein the at least one pulse includes a plurality of stimulation pulses.

11. The method of claim 1, further comprising implanting one or more electrodes into the subject's brain.

* * * * *